United States Patent
Sweeney

(10) Patent No.: US 8,344,315 B2
(45) Date of Patent: Jan. 1, 2013

(54) PROCESS FOR RAPIDLY FINDING THE ACCURATE MASSES OF SUBFRAGMENTS COMPRISING AN UNKNOWN COMPOUND FROM THE ACCURATE-MASS MASS SPECTRAL DATA OF THE UNKNOWN COMPOUND OBTAINED ON A MASS SPECTROMETER

(75) Inventor: Daniel Leo Sweeney, Arlington Heights, IL (US)

(73) Assignee: Math Spec, Inc., Arlington Heights, IL (US)

( * ) Notice: Subject to any disclaimer, the term of this patent is extended or adjusted under 35 U.S.C. 154(b) by 289 days.

(21) Appl. No.: 12/802,021

(22) Filed: May 27, 2010

(65) Prior Publication Data

US 2011/0290993 A1 Dec. 1, 2011

(51) Int. Cl.
*H01J 49/26* (2006.01)
(52) U.S. Cl. ............ 250/282; 250/287; 700/28; 700/33; 702/27; 702/28; 702/127; 702/134
(58) Field of Classification Search .................. 250/281, 250/282, 287; 700/28, 33; 702/19, 22, 23, 702/24, 26, 27, 28, 29, 127, 134
See application file for complete search history.

(56) References Cited

U.S. PATENT DOCUMENTS

2003/0036207 A1* 2/2003 Washburn et al. ............ 436/518

2006/0249667 A1* 11/2006 Goldberg et al. ............. 250/281

OTHER PUBLICATIONS

D. L. Sweeney "Small Molecules As Mathematical Partitions", Analytical Chemistry 2001 75(20), pp. 5362-5373.
Q. Wu "Multistage Accurate Mass Spectrometry: a "Basket-in-a-Basket" Approach . . . " Analytical Chemistry 1998 70 pp. 865-872.
T. Kind "Using GC-MS, LC-MS, and FT-ICR-MS data for structure elucidation . . . " Oral Presentation at CoSMoS Annual Meeting, Jul. 2008.
http://en.wikipedia.org/wiki/Sun Cloud.
D.L. Sweeney "A Systematic Computational Approach for Identifying Small Molecules from Accurate-Mass Computational Data" Americal Laboratory News, 2007, vol. 37(17) pp. 12-14.
I.A. Watson, A. Mahoui, D.C. Duckworth, D. A. Peake "A strategy for structure confirmation of drug molecules . . . " 53rd ASMS Conference on Mass Spectrometry, Jun. 2005.
A. Hill and R. Mortishire-Smith "Automated Assignment of High-Resolution Collisionally Activated Mass Spectra . . . " Rapid Commun. Mass Spectro. 2005, 19, pp. 3111-3118.
R.A. Rourick, K.J. Volk, S.E. Klohr, T. Spears, E.H. Kerns, M.S. Lee "Predictive Strategy for the Rapid Structure Elucidation . . . " Pharm. Biomed. Anal. 1996, 14, 1743-1752.

* cited by examiner

*Primary Examiner* — David A Vanore
*Assistant Examiner* — Nicole Ippolito

(57) ABSTRACT

The invention is a process for finding the accurate masses of subfragments comprising an unknown compound from the accurate-mass mass spectral data of the unknown compound obtained on a mass spectrometer. This process generates these accurate masses of subfragments using mass differences of fragment ions and a listing of plausible masses. In this way, the accurate masses of subfragments, useful for generating modular structures, can be obtained very rapidly.

1 Claim, 1 Drawing Sheet

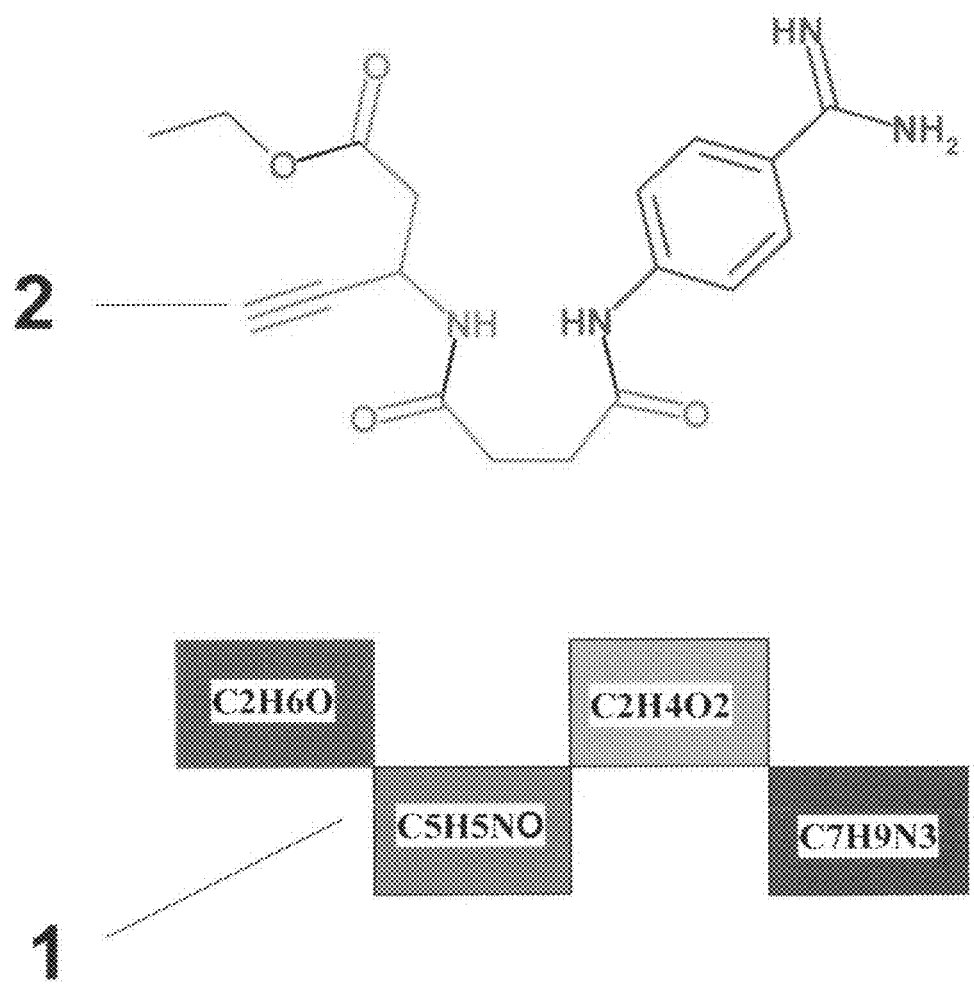

PROCESS FOR RAPIDLY FINDING THE ACCURATE MASSES OF SUBFRAGMENTS COMPRISING AN UNKNOWN COMPOUND FROM THE ACCURATE-MASS MASS SPECTRAL DATA OF THE UNKNOWN COMPOUND OBTAINED ON A MASS SPECTROMETER

CROSS REFERENCE TO RELATED APPLICATIONS

USPTO 61/217,191

FEDERALLY SPONSORED RESEARCH

Not Applicable

FIELD OF THE INVENTION

The invention comprises:

a process for finding the accurate masses of subfragments comprising an unknown compound from the accurate-mass mass spectral data of the unknown compound obtained on a mass spectrometer, whereby accurate masses of subfragments, useful for searching databases and generating modular structures, can be obtained more rapidly.

BACKGROUND

Prior Art

The following is a tabulation of prior art that appears relevant
1. Sweeney, D. L., Small Molecules As Mathematical Partitions. Anal. Chem. 2003, 75(20), 5362-5373.
2. Wu, Q. Multistage accurate mass spectrometry: a "basket in a basket" approach for structure elucidation and its application to a compound from combinatorial synthesis. Anal. Chem. 1998, 70, 865-72.
3. Tobias Kind, Using GC-MS, LC-MS and FT-ICR-MS data for structure elucidation of small molecules. Oral presentation at CoSMoS 2007, Society for Small Molecule Science Annual Meeting. San Jose, Calif. Jul. 28, 2008.
4. (http://en.wikipedia.org/wiki/Sun_Cloud).
5. D. L. Sweeney American Laboratory News, 2007, vol. 39 (17), pp. 12-14.
6. Watson, I. A.; Mahoui, A.; Duckworth, D. C.; Peake, D. A. A strategy for structure confirmation of drug molecules via automated matching of structures with exact mass MS/MS spectra. Proceedings of the 53rd ASMS Conference on Mass Spectrometry, Jun. 5-9, 2005, San Antonio, Tex.
7. Hill, A.; Mortishire-Smith, R. Automated assignment of high-resolution collisionally activated dissociation mass spectra using a systematic bond disconnection approach. Rapid Commun. Mass Spectrom. 2005, 19, 3111-18.
8. Rourick, R. A.; Volk, K. J.; Klohr, S. E.; Spears, T.; Kerns, E. H.; Lee, M. S. Predictive strategy for the rapid structure elucidation of drug degradants. Pharm. Biomed. Anal. 1996, 14, 1743-52.

BACKGROUND

Methods for rapidly identifying unknown compounds from their corresponding mass spectra have been evolving. Sweeney (2003) described in great detail a process for deriving modular structures directly from CID-type accurate-mass mass spectral data; this process will herein be called partitioning. Modular structures obtained by partitioning basically show how mass spectral fragments may be related to one another. Many small organic compounds can be represented in the form of unbreakable cells or subfragments, of known elemental composition, joined together at cleavable seams. These representations are called modular structures. Modular structures are a convenient way of summarizing and viewing CID-type mass spectral data. Each modular structure has a unique molecular formula. The fragment ions are viewed as different sets of connected subfragments; each subfragment has an elemental composition that is complementary to all of the other subfragments composing the modular structure. For example, if a plausible elemental composition of the whole molecule has only one sulfur atom, then assigning that sulfur atom to one particular subfragment will preclude all of other subfragments from having a sulfur atom.

In contrast to Wu's basket-in-a-basket approach that also can yield structural information, partitioning does not require accurate mass $MS^4$ or $MS^5$ data, obtained with difficulty on expensive instruments, such as FT-ICR mass spectrometers. In addition, partitioning can often yield spatial information about how the subfragments are arranged in the modular structure, whereas the basket-in-a-basket approach yields little spatial information. Because there are usually more fragments than subfragments, the calculated mass defects of the subfragments will often be more accurate than the fragment ion masses since the subfragments are "weighed" in combinations rather than one at a time (Sweeney 2003). The partitioning approach is also conceptually simple; it has few "rules"—in contrast to some competitive expert system software. For example, Mass Frontier now has about 20000 rules according to Kind.

Modular structures differ from molecular structures in two ways. First, the number of hydrogens in a particular subfragment of the modular structure will often differ from the number of hydrogens in the corresponding part of the molecular structure. However, the non-hydrogen atoms (herein called heavy atoms) are present in equal numbers (Drawing). In addition, while the heavy atoms of the subfragments are usually present in exactly the same combinations found in corresponding parts of the molecular structure, there is a lack of atomic sequence information in the modular structures. For example, one subfragment of the modular structure of xemilofiban (Drawing, blue color) is a combination of atoms (C2H6O), which corresponds to the ethoxy moiety (—O—CH2-CH3) in xemilofiban. Ignoring the hydrogens, the same combination of atoms (C2O) is present in both the modular structure and the molecular structure. However, while the combinations of elements are the same, the molecular structure has a specific ordering of atoms (—O—C—C) that is lacking in the modular structures.

Rational Numbers® partitioning software was commercially available in an Apple Mac mini format from December 2006 to December 2007; it was later available on The Sun Grid Compute Utility, also called the Sun Cloud in the wikipedia, from April 2007 until October 2008 when Sun closed the Sun Grid compute utility in a cost-cutting move.

How Partitioning has been Used (Sweeney 2007)
1. De Novo Identification of a Novel Compound (Rational Numbers® Partition)

With limited background information, it is extremely difficult to identify a novel compound from mass spectral data. However, combined with NMR data, the complete molecular structure can often be derived. NMR is very useful for determining which atom is connected to which atom, but sometimes there are gaps (substructures with no hydrogens or carbons) in a compound. In a sense, mass spectrometry shows the clumps of trees in the whole forest, whereas NMR shows exactly how the trees are arranged in each clump.

In the case of de novo identification, the 10 modular structures best accounting for the mass spectral data are saved. These modular structures give a rough idea of the overall structure of the compound. Some modular structures will fit the data very well, but may not correspond well to the actual molecular structure. Although the modular structures are ranked, there is no way of knowing a priori which ones match the structure of the compound that produced the spectral data and which ones do not. For de novo identification work, modular structures with up to five subfragments have been used.

2. Identification Using the "Template" Approach (Rational Numbers® Assign)

In the pharmaceutical industry, unknown compounds are usually closely related to a lead compound: degradation products, impurities, or metabolites. Traditionally, the mass spectral data of that lead compound are used to work out the fragmentation pathways, and the unknown compounds are then identified based on the changes in the masses of various fragments. This approach works well, but it can be very time consuming.

Watson et al. and Hill et al. used systematic bond-disconnection to assign accurate-mass fragments to known compounds. A similar approach is used to assign subfragments of modular structures to specific molecular subgroups of a lead compound. The heavy atom distribution of modular structures, derived from the mass spectral data, is compared to the heavy atom distribution of a computerized molecular structure of the lead compound to find matches. Only the modular structures that correlate with the computerized molecular structure are saved, and a monochrome molecular structure can then be color-coded with the same color scheme as the modular structures. This makes the fragmentation easy to visualize.

By using the modular structures that match the lead compound as templates, related unknown compounds can now be identified by comparing modular structures to modular structures. The modular structures of the unknown compound that best match the templates are saved and linked to the template modular structure that they most closely match. For correlating related compounds to a lead compound of known structure using the template approach described by Rourick et al., subfragments are clearly the most simple units of comparison.

3. Identification by Matching Compounds (Rational Numbers® FragSearch and IndexSearch)

The basic approach used to assign subfragments and fragments to a single template compound, systematic bond-disconnection, and comparison of the heavy atom distributions has been applied to searching molecular structure databases. Traditional spectral libraries are not needed. A set of modular structures are derived from the mass spectral data, and then this set of modular structures is compared to all computerized molecular structures in the database that have a similar mass. Computerized molecular structures that match modular structures are then ranked according to how many modular structures are matched and the scores of the matching modular structures. The overall objective is to draw a rough picture of molecules that would correlate with the accurate mass fragmentation data, and then to search through an index of the MDL® (now Symyx) Available Chemicals Directory or PubChem to find matching compounds. For searching, modular structures with up to four subfragments have been used. The searching was done by comparing the heavy atom compositions of subfragments to the heavy atom compositions of subgroups generated by applying systematic bond disconnection to a computerized molecular structure. The distribution of RDEs (ring and double-bond equivalents) was also compared.

Determining modular structures from mass spectral data requires finding the accurate masses of the subfragments, determining the elemental compositions of the subfragments, and finding a way to connect the subfragments together in a manner consistent with all of the mass spectral data. This invention deals with finding the accurate masses of the subfragments.

Prior Art Used to Determine the Accurate Masses of Subfragments

The spectral ions are neutralized by adding the mass of a proton to negative ions and subtracting the mass of a proton from positive ions. Positive and negative ion data are then pooled. This procedure of neutralizing ions is performed on all data sets, prior to finding the subfragment masses.

Accurate masses of subfragments are currently found in a four step process (Sweeney 2003):

Step 1: Partitions of the integral molecular weight are found. A partition is a mathematical term for a set of integers that sum up to another integer. For each partition, every combination of those integers is then summed to select those partitions that best account for the fragment masses.

Step 2: Fragment masses are then "assigned" as sums of different combinations of the individual integers. The individual integers can be viewed as the integral masses of subfragments; assigned fragments are then sums of subfragments. A score based on coverage (weighted intensity) of each assigned ion is also calculated.

Step 3. Partitions with "linked subfragments" are then removed. Linked subfragments are basically trivial solutions in which a subfragment has been divided into two subfragments that always are assigned together.

Step 4: The fragments have been assigned as integral sums of various combinations of subfragments. The mass defects of the subfragments that compose any particular fragment must also sum up to the mass defect of that fragment. Since the mass defects of the fragments are known, the mass defects of the subfragments can be calculated by solving a set of simultaneous linear equations.

At this point we have a score and a set of subfragment accurate masses for each partition. The current process for finding accurate masses of subfragments is CPU intensive and therefore time-consuming.

Partitioning is very CPU intensive and this has limited its development because most potential improvements would also significantly increase the CPU requirements. As an illustration, the data for xemilofiban, which was an example in the 2003 Sweeney paper, will be used. The masses of the subfragments of 4-subfragment partitions were found.

The accurate-mass MS/MS data for xemilofiban in the paper has 12 fragments, including the protonated molecule. The molecular weight is 358. For this molecular weight, depending on the starting mass, there are 151559 possible integral partitions of 4 subfragments. Generating these 151559 partitions took 6 milliseconds (step 1). Finding partitions having a score greater than 57 (arbitrary score chosen for comparison purposes) took another 253 milliseconds (step 2). The most CPU intensive operation was calculating the mass defects using the multi-stage Monte Carlo optimization (MSMCO) to solve the simultaneous equations. The 169 MSMCO optimizations that were done took 10237 milliseconds (step 3), roughly 61 milliseconds each. This gave a total time of 10496 milliseconds. This does not include any operations to determine possible spatial arrangements of the subfragments or to find elemental compositions of the subfragments.

| Total Partitions 151559 | | | | |
|---|---|---|---|---|
| Score | A | B | C | D |
| 58 | 170264 | 189376 | 1410789 | 1811214 |
| 58 | 170265 | 359641 | 1410789 | 1640948 |
| 58 | 170265 | 400425 | 1410788 | 1600165 |
| 70 | 170267 | 649791 | 1350798 | 1410790 |
| 73 | 170270 | 820063 | 1180525 | 1410787 |
| 61 | 170264 | 820058 | 1240526 | 1350797 |
| 58 | 189377 | 400424 | 1410789 | 1581053 |
| 61 | 339853 | 480205 | 1350797 | 1410790 |
| 61 | 359642 | 419630 | 991158 | 1811213 |
| 70 | 359639 | 460420 | 1350796 | 1410790 |
| 61 | 359645 | 820056 | 991155 | 1410785 |
| 61 | 360464 | 820058 | 1050326 | 1350798 |
| 61 | 380498 | 970302 | 1030288 | 1200554 |
| 67 | 400426 | 419634 | 1350797 | 1410788 |
| 67 | 400426 | 460419 | 950370 | 1770430 |
| 73 | 400429 | 820059 | 950368 | 1410789 |
| 58 | 401173 | 820058 | 1009617 | 1350797 |
| 58 | 420467 | 820059 | 930330 | 1410789 |
| 61 | 419630 | 820055 | 991158 | 1350800 |
| 73 | 460421 | 820059 | 950369 | 1350797 |
| 61 | 480204 | 820058 | 930586 | 1350797 |
| 58 | 530736 | 820064 | 820055 | 1410788 |
| 58 | 530737 | 820063 | 880051 | 1350792 |
| 61 | 589805 | 649790 | 760995 | 1581052 |
| 61 | 589803 | 760997 | 820056 | 1410787 |
| 58 | 590731 | 820059 | 820058 | 1350797 |
| 58 | 596609 | 814181 | 820058 | 1350797 |
| 61 | 649788 | 760998 | 820055 | 1350801 | bolded partitions above correlate well with the molecular structure

The basic problem with the present approach for generating modular structures is that the process is very CPU intensive and therefore time-consuming, especially as the molecular weight increases and the number of subfragments increases (e.g. a 5-subfragment set of masses takes much much longer to find than a 4-subfragment set of masses). More computer power is very helpful; using a computer cluster such as the Sun Grid allows parallel processing and significantly reduces the elapsed time, but introduces the added complexity of opening and maintaining an account on a compute utility.

SUMMARY OF THE INVENTION

The invention is:
a process for finding the accurate masses of subfragments comprising an unknown compound from the accurate-mass mass spectral data of the unknown compound obtained on a mass spectrometer,
whereby accurate masses of subfragments, useful for generating modular structures, can be obtained more rapidly.

DRAWING

A modular structure of xemilofiban (1) is compared to a molecular structure (2).

DETAILED DESCRIPTION OF THE INVENTION

To explain the invention in detail, the accurate-mass fragmentation data of xemilofiban will be taken through the entire process. This compound was also an example in the Analytical Chemistry paper using prior art. In this specific example, finding the accurate masses of a 4-subfragment partition of xemilofiban will be demonstrated. Partitions with various numbers of subfragments (2-subfragment, 3-subfragment, 5-subfragment, 6-subfragment, etc.) can be obtained in a similar fashion. All programs were written in the C programming language and CPU times were measured on a Mac mini with an Intel Core Solo CPU running at 1.5 Mhz.

The process starts with obtaining accurate-mass fragmentation data on a mass spectrometer. The fragment ions obtained on the mass spectrometer are then neutralized by adding the mass of a proton to negative ions and subtracting the mass of a proton from positive ions. Positive and negative ion data are then pooled when both positive and negative ion fragmentation data are available. After neutralization of the experimentally determined fragment masses, the following twelve masses below were obtained for xemilofiban, which has an integral molecular weight of 358; the small integers under the accurate masses are the experimentally determined intensities (the intensity of 358.1642 (the whole molecule) is forced to be 0).

| |
|---|
| 95.0367 |
| 2 |
| 118.0522 |
| 2 |
| 124.0525 |
| 3 |
| 135.0800 |
| 47 |
| 141.0790 |
| 2 |
| 175.0643 |
| 3 |
| 177.0430 |
| 17 |
| 200.0590 |
| 19 |
| 216.1018 |
| 2 |
| 217.0856 |
| 100 |
| 223.0851 |
| 6 |
| 358.1642 |
| 0 |

Next determine the $0^{th}$, $1^{st}$, and $2^{nd}$ order differences of the fragment ions. These are the possible subfragment masses. (For the convenience of working with integers, fragment masses were multiplied by 10000 to convert them into units of tenths of millidaltons.)

Zero order differences are the accurate masses of the neutralized fragment ions and the neutralized molecule. For xemilofiban:
A zero order difference is: 950367
A zero order difference is: 1180522
A zero order difference is: 1240525
A zero order difference is: 1350800
A zero order difference is: 1410790
A zero order difference is: 1750643
A zero order difference is: 1770430
A zero order difference is: 2000590
A zero order difference is: 2161018
A zero order difference is: 2170856
A zero order difference is: 2230851
A zero order difference is: 3581642
First order differences are the differences between every combination of two fragment ions.

| | | | | | |
|---|---|---|---|---|---|
| Frag1: | 1180522 | Frag2 | 950367 | A first order difference is: | 230155 |
| Frag1: | 1240525 | Frag2 | 950367 | A first order difference is: | 290158 |
| Frag1: | 1350800 | Frag2 | 950367 | A first order difference is: | 400433 |
| Frag1: | 1410790 | Frag2 | 950367 | A first order difference is: | 460423 |
| Frag1: | 1750643 | Frag2 | 950367 | A first order difference is: | 800276 |
| Frag1: | 1770430 | Frag2 | 950367 | A first order difference is: | 820063 |
| Frag1: | 2000590 | Frag2 | 950367 | A first order difference is: | 1050223 |
| Frag1: | 2161018 | Frag2 | 950367 | A first order difference is: | 1210651 |
| Frag1: | 2170856 | Frag2 | 950367 | A first order difference is: | 1220489 |
| Frag1: | 2230851 | Frag2 | 950367 | A first order difference is: | 1280484 |
| Frag1: | 3581642 | Frag2 | 950367 | A first order difference is: | 2631275 |
| Frag1: | 1240525 | Frag2 | 1180522 | A first order difference is: | 60003 |
| Frag1: | 1350800 | Frag2 | 1180522 | A first order difference is: | 170278 |
| Frag1: | 1410790 | Frag2 | 1180522 | A first order difference is: | 230268 |
| Frag1: | 1750643 | Frag2 | 1180522 | A first order difference is: | 570121 |
| Frag1: | 1770430 | Frag2 | 1180522 | A first order difference is: | 589908 |
| Frag1: | 2000590 | Frag2 | 1180522 | A first order difference is: | 820068 |
| Frag1: | 2161018 | Frag2 | 1180522 | A first order difference is: | 980496 |
| Frag1: | 2170856 | Frag2 | 1180522 | A first order difference is: | 990334 |
| Frag1: | 2230851 | Frag2 | 1180522 | A first order difference is: | 1050329 |
| Frag1: | 3581642 | Frag2 | 1180522 | A first order difference is: | 2401120 |
| Frag1: | 1350800 | Frag2 | 1240525 | A first order difference is: | 110275 |
| Frag1: | 1410790 | Frag2 | 1240525 | A first order difference is: | 170265 |
| Frag1: | 1750643 | Frag2 | 1240525 | A first order difference is: | 510118 |
| Frag1: | 1770430 | Frag2 | 1240525 | A first order difference is: | 529905 |
| Frag1: | 2000590 | Frag2 | 1240525 | A first order difference is: | 760065 |
| Frag1: | 2161018 | Frag2 | 1240525 | A first order difference is: | 920493 |
| Frag1: | 2170856 | Frag2 | 1240525 | A first order difference is: | 930331 |
| Frag1: | 2230851 | Frag2 | 1240525 | A first order difference is: | 990326 |
| Frag1: | 3581642 | Frag2 | 1240525 | A first order difference is: | 2341117 |
| Frag1: | 1410790 | Frag2 | 1350800 | A first order difference is: | 59990 |
| Frag1: | 1750643 | Frag2 | 1350800 | A first order difference is: | 399843 |
| Frag1: | 1770430 | Frag2 | 1350800 | A first order difference is: | 419630 |
| Frag1: | 2000590 | Frag2 | 1350800 | A first order difference is: | 649790 |
| Frag1: | 2161018 | Frag2 | 1350800 | A first order difference is: | 810218 |
| Frag1: | 2170856 | Frag2 | 1350800 | A first order difference is: | 820056 |
| Frag1: | 2230851 | Frag2 | 1350800 | A first order difference is: | 880051 |
| Frag1: | 3581642 | Frag2 | 1350800 | A first order difference is: | 2230842 |
| Frag1: | 1750643 | Frag2 | 1410790 | A first order difference is: | 339853 |
| Frag1: | 1770430 | Frag2 | 1410790 | A first order difference is: | 359640 |
| Frag1: | 2000590 | Frag2 | 1410790 | A first order difference is: | 589800 |
| Frag1: | 2161018 | Frag2 | 1410790 | A first order difference is: | 750228 |
| Frag1: | 2170856 | Frag2 | 1410790 | A first order difference is: | 760066 |
| Frag1: | 2230851 | Frag2 | 1410790 | A first order difference is: | 820061 |
| Frag1: | 3581642 | Frag2 | 1410790 | A first order difference is: | 2170852 |
| Frag1: | 1770430 | Frag2 | 1750643 | A first order difference is: | 19787 |
| Frag1: | 2000590 | Frag2 | 1750643 | A first order difference is: | 249947 |
| Frag1: | 2161018 | Frag2 | 1750643 | A first order difference is: | 410375 |
| Frag1: | 2170856 | Frag2 | 1750643 | A first order difference is: | 420213 |
| Frag1: | 2230851 | Frag2 | 1750643 | A first order difference is: | 480208 |
| Frag1: | 3581642 | Frag2 | 1750643 | A first order difference is: | 1830999 |
| Frag1: | 2000590 | Frag2 | 1770430 | A first order difference is: | 230160 |
| Frag1: | 2161018 | Frag2 | 1770430 | A first order difference is: | 390588 |
| Frag1: | 2170856 | Frag2 | 1770430 | A first order difference is: | 400426 |
| Frag1: | 2230851 | Frag2 | 1770430 | A first order difference is: | 460421 |
| Frag1: | 3581642 | Frag2 | 1770430 | A first oder difference is: | 1811212 |
| Frag1: | 2161018 | Frag2 | 2000590 | A first order difference is: | 160428 |
| Frag1: | 2170856 | Frag2 | 2000590 | A first order difference is: | 170266 |
| Frag1: | 2230851 | Frag2 | 2000590 | A first order difference is: | 230261 |
| Frag1: | 3581642 | Frag2 | 2000590 | A first order difference is: | 1581052 |
| Frag1: | 2170856 | Frag2 | 2161018 | A first order difference is: | 9838 |
| Frag1: | 2230851 | Frag2 | 2161018 | A first order difference is: | 69833 |
| Frag1: | 3581642 | Frag2 | 2161018 | A first order difference is: | 1420624 |
| Frag1: | 2230851 | Frag2 | 2170856 | A first order difference is: | 59995 |
| Frag1: | 3581642 | Frag2 | 2170856 | A first order difference is: | 1410786 |
| Frag1: | 3581642 | Frag2 | 2230851 | A first order difference is: | 1350791 |

The $2^{nd}$ order differences are obtained by adding two fragment masses and subtracting a third. For xemilofiban the second order differences are shown below. The fragment ions in the first two columns are summed and then the fragment in the third column is subtracted, giving the possible subfragment mass in the fourth column. The differences listed are all absolute values of differences so all masses in the list are positive integers.

| | | | | |
|---|---|---|---|---|
| A second order difference is: | 950367 | 1180522 | 1240525 | 890364 |
| A second order difference is: | 950367 | 1180522 | 1350800 | 780089 |
| A second order difference is: | 950367 | 1180522 | 1410790 | 720099 |

| | | | | |
|---|---|---|---|---|
| A second order difference is: | 950367 | 1180522 | 1750643 | 380246 |
| A second order difference is: | 950367 | 1180522 | 1770430 | 360459 |
| A second order difference is: | 950367 | 1180522 | 2000590 | 130299 |
| A second order difference is: | 950367 | 1180522 | 2161018 | 30129 |
| A second order difference is: | 950367 | 1180522 | 2170856 | 39967 |
| A second order difference is: | 950367 | 1180522 | 2230851 | 99962 |
| A second order difference is: | 950367 | 1180522 | 3581642 | 1450753 |
| A second order difference is: | 950367 | 1240525 | 1350800 | 840092 |
| A second order difference is: | 950367 | 1240525 | 1410790 | 780102 |
| A second order difference is: | 950367 | 1240525 | 1750643 | 440249 |
| A second order difference is: | 950367 | 1240525 | 1770430 | 420462 |
| A second order difference is: | 950367 | 1240525 | 2000590 | 190302 |
| A second order difference is: | 950367 | 1240525 | 2161018 | 29874 |
| A second order difference is: | 950367 | 1240525 | 2170856 | 20036 |
| A second order difference is: | 950367 | 1240525 | 2230851 | 39959 |
| A second order difference is: | 950367 | 1240525 | 3581642 | 1390750 |
| A second order difference is: | 950367 | 1350800 | 1410790 | 890377 |
| A second order difference is: | 950367 | 1350800 | 1750643 | 550524 |
| A second order difference is: | 950367 | 1350800 | 1770430 | 530737 |
| A second order difference is: | 950367 | 1350800 | 2000590 | 300577 |
| A second order difference is: | 950367 | 1350800 | 2161018 | 140149 |
| A second order difference is: | 950367 | 1350800 | 2170856 | 130311 |
| A second order difference is: | 950367 | 1350800 | 2230851 | 70316 |
| A second order difference is: | 950367 | 1350800 | 3581642 | 1280475 |
| A second order difference is: | 950367 | 1410790 | 1750643 | 610514 |
| A second order difference is: | 950367 | 1410790 | 1770430 | 590727 |
| A second order difference is: | 950367 | 1410790 | 2000590 | 360567 |
| A second order difference is: | 950367 | 1410790 | 2161018 | 200139 |
| A second order difference is: | 950367 | 1410790 | 2170856 | 190301 |
| A second order difference is: | 950367 | 1410790 | 2230851 | 130306 |
| A second order difference is: | 950367 | 1410790 | 3581642 | 1220485 |
| A second order difference is: | 950367 | 1750643 | 1770430 | 930580 |
| A second order difference is: | 950367 | 1750643 | 2000590 | 700420 |
| A second order difference is: | 950367 | 1750643 | 2161018 | 539992 |
| A second order difference is: | 950367 | 1750643 | 2170856 | 530154 |
| A second order difference is: | 950367 | 1750643 | 2230851 | 470159 |
| A second order difference is: | 950367 | 1750643 | 3581642 | 880632 |
| A second order difference is: | 950367 | 1770430 | 2000590 | 720207 |
| A second order difference is: | 950367 | 1770430 | 2161018 | 559779 |
| A second order difference is: | 950367 | 1770430 | 2170856 | 549941 |
| A second order difference is: | 950367 | 1770430 | 2230851 | 489946 |
| A second order difference is: | 950367 | 1770430 | 3581642 | 860845 |
| A second order difference is: | 950367 | 2000590 | 2161018 | 789939 |
| A second order difference is: | 950367 | 2000590 | 2170856 | 780101 |
| A second order difference is: | 950367 | 2000590 | 2230851 | 720106 |
| A second order difference is: | 950367 | 2000590 | 3581642 | 630685 |
| A second order difference is: | 950367 | 2161018 | 2170856 | 940529 |
| A second order difference is: | 950367 | 2161018 | 2230851 | 880534 |
| A second order difference is: | 950367 | 2161018 | 3581642 | 470257 |
| A second order difference is: | 950367 | 2170856 | 2230851 | 890372 |
| A second order difference is: | 950367 | 2170856 | 3581642 | 460419 |
| A second order difference is: | 950367 | 2230851 | 3581642 | 400424 |
| A second order difference is: | 1180522 | 1240525 | 1350800 | 1070247 |
| A second order difference is: | 1180522 | 1240525 | 1410790 | 1010257 |
| A second order difference is: | 1180522 | 1240525 | 1750643 | 670404 |
| A second order difference is: | 1180522 | 1240525 | 1770430 | 650617 |
| A second order difference is: | 1180522 | 1240525 | 2000590 | 420457 |
| A second order difference is: | 1180522 | 1240525 | 2161018 | 260029 |
| A second order difference is: | 1180522 | 1240525 | 2170856 | 250191 |
| A second order difference is: | 1180522 | 1240525 | 2230851 | 190196 |
| A second order difference is: | 1180522 | 1240525 | 3581642 | 1160595 |
| A second order difference is: | 1180522 | 1350800 | 1410790 | 1120532 |
| A second order difference is: | 1180522 | 1350800 | 1750643 | 780679 |
| A second order difference is: | 1180522 | 1350800 | 1770430 | 760892 |
| A second order difference is: | 1180522 | 1350800 | 2000590 | 530732 |
| A second order difference is: | 1180522 | 1350800 | 2161018 | 370304 |
| A second order difference is: | 1180522 | 1350800 | 2170856 | 360466 |
| A second order difference is: | 1180522 | 1350800 | 2230851 | 300471 |
| A second order difference is: | 1180522 | 1350800 | 3581642 | 1050320 |
| A second order difference is: | 1180522 | 1410790 | 1750643 | 840669 |
| A second order difference is: | 1180522 | 1410790 | 1770430 | 820882 |
| A second order difference is: | 1180522 | 1410790 | 2000590 | 590722 |
| A second order difference is: | 1180522 | 1410790 | 2161018 | 430294 |
| A second order difference is: | 1180522 | 1410790 | 2170856 | 420456 |
| A second order difference is: | 1180522 | 1410790 | 2230851 | 360461 |
| A second order difference is: | 1180522 | 1410790 | 3581642 | 990330 |
| A second order difference is: | 1180522 | 1750643 | 1770430 | 1160735 |
| A second order difference is: | 1180522 | 1750643 | 2000590 | 930575 |
| A second order difference is: | 1180522 | 1750643 | 2161018 | 770147 |
| A second order difference is: | 1180522 | 1750643 | 2170856 | 760309 |

-continued

| | | | | |
|---|---|---|---|---|
| A second order difference is: | 1180522 | 1750643 | 2230851 | 700314 |
| A second order difference is: | 1180522 | 1750643 | 3581642 | 650477 |
| A second order difference is: | 1180522 | 1770430 | 2000590 | 950362 |
| A second order difference is: | 1180522 | 1770430 | 2161018 | 789934 |
| A second order difference is: | 1180522 | 1770430 | 2170856 | 780096 |
| A second order difference is: | 1180522 | 1770430 | 2230851 | 720101 |
| A second order difference is: | 1180522 | 1770430 | 3581642 | 630690 |
| A second order difference is: | 1180522 | 2000590 | 2161018 | 1020094 |
| A second order difference is: | 1180522 | 2000590 | 2170856 | 1010256 |
| A second order difference is: | 1180522 | 2000590 | 2230851 | 950261 |
| A second order difference is: | 1180522 | 2000590 | 3581642 | 400530 |
| A second order difference is: | 1180522 | 2161018 | 2170856 | 1170684 |
| A second order difference is: | 1180522 | 2161018 | 2230851 | 1110689 |
| A second order difference is: | 1180522 | 2161018 | 3581642 | 240102 |
| A second order difference is: | 1180522 | 2170856 | 2230851 | 1120527 |
| A second order difference is: | 1180522 | 2170856 | 3581642 | 230264 |
| A second order difference is: | 1180522 | 2230851 | 3581642 | 170269 |
| A second order difference is: | 1240525 | 1350800 | 1410790 | 1180535 |
| A second order difference is: | 1240525 | 1350800 | 1750643 | 840682 |
| A second order difference is: | 1240525 | 1350800 | 1770430 | 820895 |
| A second order difference is: | 1240525 | 1350800 | 2000590 | 590735 |
| A second order difference is: | 1240525 | 1350800 | 2161018 | 430307 |
| A second order difference is: | 1240525 | 1350800 | 2170856 | 420469 |
| A second order difference is: | 1240525 | 1350800 | 2230851 | 360474 |
| A second order difference is: | 1240525 | 1350800 | 3581642 | 990317 |
| A second order difference is: | 1240525 | 1410790 | 1750643 | 900672 |
| A second order difference is: | 1240525 | 1410790 | 1770430 | 880885 |
| A second order difference is: | 1240525 | 1410790 | 2000590 | 650725 |
| A second order difference is: | 1240525 | 1410790 | 2161018 | 490297 |
| A second order difference is: | 1240525 | 1410790 | 2170856 | 480459 |
| A second order difference is: | 1240525 | 1410790 | 2230851 | 420464 |
| A second order difference is: | 1240525 | 1410790 | 3581642 | 930327 |
| A second order difference is: | 1240525 | 1750643 | 1770430 | 1220738 |
| A second order difference is: | 1240525 | 1750643 | 2000590 | 990578 |
| A second order difference is: | 1240525 | 1750643 | 2161018 | 830150 |
| A second order difference is: | 1240525 | 1750643 | 2170856 | 820312 |
| A second order difference is: | 1240525 | 1750643 | 2230851 | 760317 |
| A second order difference is: | 1240525 | 1750643 | 3581642 | 590474 |
| A second order difference is: | 1240525 | 1770430 | 2000590 | 1010365 |
| A second order difference is: | 1240525 | 1770430 | 2161018 | 849937 |
| A second order difference is: | 1240525 | 1770430 | 2170856 | 840099 |
| A second order difference is: | 1240525 | 1770430 | 2230851 | 780104 |
| A second order difference is: | 1240525 | 1770430 | 3581642 | 570687 |
| A second order difference is: | 1240525 | 2000590 | 2161018 | 1080097 |
| A second order difference is: | 1240525 | 2000590 | 2170856 | 1070259 |
| A second order difference is: | 1240525 | 2000590 | 2230851 | 1010264 |
| A second order difference is: | 1240525 | 2000590 | 3581642 | 340527 |
| A second order difference is: | 1240525 | 2161018 | 2170856 | 1230687 |
| A second order difference is: | 1240525 | 2161018 | 2230851 | 1170692 |
| A second order difference is: | 1240525 | 2161018 | 3581642 | 180099 |
| A second order difference is: | 1240525 | 2170856 | 2230851 | 1180530 |
| A second order difference is: | 1240525 | 2170856 | 3581642 | 170261 |
| A second order difference is: | 1240525 | 2230851 | 3581642 | 110266 |
| A second order difference is: | 1350800 | 1410790 | 1750643 | 1010947 |
| A second order difference is: | 1350800 | 1410790 | 1770430 | 991160 |
| A second order difference is: | 1350800 | 1410790 | 2000590 | 761000 |
| A second order difference is: | 1350800 | 1410790 | 2161018 | 600572 |
| A second order difference is: | 1350800 | 1410790 | 2170856 | 590734 |
| A second order difference is: | 1350800 | 1410790 | 2230851 | 530739 |
| A second order difference is: | 1350800 | 1410790 | 3581642 | 820052 |
| A second order difference is: | 1350800 | 1750643 | 1770430 | 1331013 |
| A second order difference is: | 1350800 | 1750643 | 2000590 | 1100853 |
| A second order difference is: | 1350800 | 1750643 | 2161018 | 940425 |
| A second order difference is: | 1350800 | 1750643 | 2170856 | 930587 |
| A second order difference is: | 1350800 | 1750643 | 2230851 | 870592 |
| A second order difference is: | 1350800 | 1750643 | 3581642 | 480199 |
| A second order difference is: | 1350800 | 1770430 | 2000590 | 1120640 |
| A second order difference is: | 1350800 | 1770430 | 2161018 | 960212 |
| A second order difference is: | 1350800 | 1770430 | 2170856 | 950374 |
| A second order difference is: | 1350800 | 1770430 | 2230851 | 890379 |
| A second order difference is: | 1350800 | 1770430 | 3581642 | 460412 |
| A second order difference is: | 1350800 | 2000590 | 2161018 | 1190372 |
| A second order difference is: | 1350800 | 2000590 | 2170856 | 1180534 |
| A second order difference is: | 1350800 | 2000590 | 2230851 | 1120539 |
| A second order difference is: | 1350800 | 2000590 | 3581642 | 230252 |
| A second order difference is: | 1350800 | 2161018 | 2170856 | 1340962 |
| A second order difference is: | 1350800 | 2161018 | 2230851 | 1280967 |
| A second order difference is: | 1350800 | 2161018 | 3581642 | 69824 |
| A second order difference is: | 1350800 | 2170856 | 2230851 | 1290805 |
| A second order difference is: | 1350800 | 2170856 | 3581642 | 59986 |

-continued

| | | | | |
|---|---|---|---|---|
| A second order difference is: | 1350800 | 2230851 | 3581642 | 9 |
| A second order difference is: | 1410790 | 1750643 | 1770430 | 1391003 |
| A second order difference is: | 1410790 | 1750643 | 2000590 | 1160843 |
| A second order difference is: | 1410790 | 1750643 | 2161018 | 1000415 |
| A second order difference is: | 1410790 | 1750643 | 2170856 | 990577 |
| A second order difference is: | 1410790 | 1750643 | 2230851 | 930582 |
| A second order difference is: | 1410790 | 1750643 | 3581642 | 420209 |
| A second order difference is: | 1410790 | 1770430 | 2000590 | 1180630 |
| A second order difference is: | 1410790 | 1770430 | 2161018 | 1020202 |
| A second order difference is: | 1410790 | 1770430 | 2170856 | 1010364 |
| A second order difference is: | 1410790 | 1770430 | 2230851 | 950369 |
| A second order difference is: | 1410790 | 1770430 | 3581642 | 400422 |
| A second order difference is: | 1410790 | 2000590 | 2161018 | 1250362 |
| A second order difference is: | 1410790 | 2000590 | 2170856 | 1240524 |
| A second order difference is: | 1410790 | 2000590 | 2230851 | 1180529 |
| A second order difference is: | 1410790 | 2000590 | 3581642 | 170262 |
| A second order difference is: | 1410790 | 2161018 | 2170856 | 1400952 |
| A second order difference is: | 1410790 | 2161018 | 2230851 | 1340957 |
| A second order difference is: | 1410790 | 2161018 | 3581642 | 9834 |
| A second order difference is: | 1410790 | 2170856 | 2230851 | 1350795 |
| A second order difference is: | 1410790 | 2170856 | 3581642 | 4 |
| A second order difference is: | 1410790 | 2230851 | 3581642 | 59999 |
| A second order difference is: | 1750643 | 1770430 | 2000590 | 1520483 |
| A second order difference is: | 1750643 | 1770430 | 2161018 | 1360055 |
| A second order difference is: | 1750643 | 1770430 | 2170856 | 1350217 |
| A second order difference is: | 1750643 | 1770430 | 2230851 | 1290222 |
| A second order difference is: | 1750643 | 1770430 | 3581642 | 60569 |
| A second order difference is: | 1750643 | 2000590 | 2161018 | 1590215 |
| A second order difference is: | 1750643 | 2000590 | 2170856 | 1580377 |
| A second order difference is: | 1750643 | 2000590 | 2230851 | 1520382 |
| A second order difference is: | 1750643 | 2000590 | 3581642 | 169591 |
| A second order difference is: | 1750643 | 2161018 | 2170856 | 1740805 |
| A second order difference is: | 1750643 | 2161018 | 2230851 | 1680810 |
| A second order difference is: | 1750643 | 2161018 | 3581642 | 330019 |
| A second order difference is: | 1750643 | 2170856 | 2230851 | 1690648 |
| A second order difference is: | 1750643 | 2170856 | 3581642 | 339857 |
| A second order difference is: | 1750643 | 2230851 | 3581642 | 399852 |
| A second order difference is: | 1770430 | 2000590 | 2161018 | 1610002 |
| A second order difference is: | 1770430 | 2000590 | 2170856 | 1600164 |
| A second order difference is: | 1770430 | 2000590 | 2230851 | 1540169 |
| A second order difference is: | 1770430 | 2000590 | 3581642 | 189378 |
| A second order difference is: | 1770430 | 2161018 | 2170856 | 1760592 |
| A second order difference is: | 1770430 | 2161018 | 2230851 | 1700597 |
| A second order difference is: | 1770430 | 2161018 | 3581642 | 349806 |
| A second order difference is: | 1770430 | 2170856 | 2230851 | 1710435 |
| A second order difference is: | 1770430 | 2170856 | 3581642 | 359644 |
| A second order difference is: | 1770430 | 2230851 | 3581642 | 419639 |
| A second order difference is: | 2000590 | 2161018 | 2170856 | 1990752 |
| A second order difference is: | 2000590 | 2161018 | 2230851 | 1930757 |
| A second order difference is: | 2000590 | 2161018 | 3581642 | 579966 |
| A second order difference is: | 2000590 | 2170856 | 2230851 | 1940595 |
| A second order difference is: | 2000590 | 2170856 | 3581642 | 589804 |
| A second order difference is: | 2000590 | 2230851 | 3581642 | 649799 |
| A second order difference is: | 2161018 | 2170856 | 2230851 | 2101023 |
| A second order difference is: | 2161018 | 2170856 | 3581642 | 750232 |
| A second order difference is: | 2161018 | 2230851 | 3581642 | 810227 |
| A second order difference is: | 2170856 | 2230851 | 3581642 | 820065 |

The subtractions generate a large number of possible subfragment masses (298). Every combination of these masses, taken four at a time (to make a 4-subfragment partition), could then be tested to see if it is a partition of the molecular weight. There are a formidable 322014330 combinations of 298 masses taken four at a time. This contrasts with the prior art, where xemilofiban had only 151559 4-subfragment integral partitions. Because of the vast number of combinations and the high probability of generating essentially duplicate answers, this approach did not initially look very promising. The prior art also seemed to teach away from using simple mass differences (0 and $1^{st}$ order) between fragments (Sweeney. 2003).

Some of the mass differences cannot represent subfragments of actual molecules. For example, the third first order difference above has a mass of 400433 which is 40.0433 daltons. Since the 135.0800 fragment ion is believed to have a formula of $C_7H_9N_3$ and the 95.0367 fragment ion is postulated to have a formula of $C_5H_5NO$, the mass of 40.0433 represents $C_2H_4N_2O_{-1}$. Usually, no subfragment or piece of any real molecule can have a negative number of atoms (three exceptions are noted later).

To exclude masses such as 400433 that are implausible, a list of plausible masses was generated. See Appendix. These are masses of plausible combinations of elements of carbon, hydrogen, nitrogen, oxygen, sulfur, phosphorus, chlorine, bromine, and fluorine with masses up to about 85 daltons.

The mass of 85 was chosen as the largest mass arbitrarily; the listing could go higher. However, as the mass increases there are more combinations of elements possible for a given accuracy and so fewer masses would be excluded by the list of plausible masses.

A few points are worth noting here. First, the list of plausible masses is somewhat arbitrary as to what masses are plausible. The numbers in this listing are not cut in stone. For example, additional elements (e.g. silicon) could be added. The RDE (ring and double-bond equivalents) for a subfragment composition must be greater than or equal to zero. So $C_3H_{10}O_1$ would not be considered. Also, certain combinations of elements would not be expected to be stable enough to be present in the same subfragment of a molecule (e.g. CHN2F, H2N3O, H4N4, CHCl, and CNOF). In addition, generally the RDE cannot exceed the number of carbon, nitrogen, oxygen, and sulfur atoms. Note that the last 3 elemental compositions in the list of plausible masses have a negative number of hydrogens; these three subfragment masses are often observed in compounds with a carbon attached to three heteroatoms. Finally, plausible masses includes the mass of a hydrogen molecule at 2.0156 daltons (but not shown in the listing).

Second, a maximum defect window parameter, which is also arbitrary, is also needed. For a Q-Tof instrument, taking into account that the masses were converted into units of tenths of milliDaltons by multiplying by 10000, it is typically set at the integral molecular weight divided by 20. For the xemilofiban example here, it is 358/20 which is 17. This parameter is called the MaxDefect window. Depending upon the accuracy of the instrument, the denominator (20) in this MaxDefect equation should be adjusted up (more accurate instrument) or down (less accurate instrument). If a possible subfragment mass is not within the MaxDefect window of a plausible mass, then that possible subfragment mass is removed from the list of possible masses of subfragments.

In this example, using a MaxDefect window of 17, of the 298 possible subfragments, 107 were not within the MaxDefect window of a plausible mass and these were removed, leaving 191 possible subfragment masses. There are 53727345 combinations of 191 masses taken 4 at a time.

After removing the masses that are outside the MaxDefect window, the remaining possible subfragment masses are then sorted in numerical order. The sorted possible subfragment masses are shown in Table 1.

The remaining possible subfragment masses are then compared to each other. Two or more possible subfragment masses that have a mass difference less than or equal to the MaxDefect are then each replaced with the average mass of these subfragments. These are the averaged subfragment masses.

Averaging has two benefits. First, there is the benefit of generating an average mass of a possible subfragment mass that is based on the experimental measurement of multiple fragment ion masses. This average would be expected to be closer to the true average than a randomly-selected individual value. Second, individual possible fragment ions, having only slightly different masses, would eventually lead to essentially duplicate partitions. Finding and removing these duplicates would be a formidable task. It will be shown later that by averaging these masses here, the generation of duplicate partitions can be avoided.

The possible subfragment mass at about 820060 can be used as an example:
Frag1: 1770430 Frag2 950367 A first order difference is: 820063
Frag1: 2000590 Frag2 1180522 A first order difference is: 820068
Frag1: 2170856 Frag2 1350800 A first order difference is: 820056
Frag1: 2230851 Frag2 1410790 A first order difference is: 820061
A second order difference is: 2170856 2230851 3581642 820065
A second order difference is: 1350800 1410790 3581642 820052

The mass of about 820060 is obtained using the following experimentally derived neutralized fragment ions: 950367, 1180522, 1350800, 1410790, 1770430, 2000590, 2170856, 2230851, and 3581642. So its average mass would be based on the masses of nine experimentally measured masses.

After averaging, the possible subfragment masses are then shown in Table 2. Of the 191 possible subfragment masses, only 124 are unique masses. However, replicates are not removed, since some subfragment masses in a partition could be identical.

TABLE 1

| Possible Subfragment Masses. |
|---|
| 140149 |
| 170261 |
| 170262 |
| 170265 |
| 170266 |
| 170269 |
| 170278 |
| 180099 |
| 260029 |
| 410375 |
| 420209 |
| 420213 |
| 420456 |
| 420457 |
| 420462 |
| 420464 |
| 420469 |
| 430294 |
| 430307 |
| 440249 |
| 460412 |
| 460419 |
| 460421 |
| 460423 |
| 470159 |
| 470257 |
| 510118 |
| 590474 |
| 590722 |
| 590727 |
| 590734 |
| 590735 |
| 600572 |
| 610514 |
| 700420 |
| 720099 |
| 720101 |
| 720207 |
| 750228 |
| 750232 |
| 760065 |
| 760066 |
| 760309 |
| 760317 |
| 770147 |
| 780089 |
| 780096 |
| 780101 |
| 780102 |
| 780104 |
| 789939 |
| 800276 |
| 810218 |
| 810227 |
| 820052 |
| 820056 |
| 820061 |
| 820063 |
| 820065 |
| 820068 |
| 840092 |
| 840099 |

TABLE 1-continued

Possible Subfragment Masses.

840682
849937
860845
870592
880051
880534
880632
880885
890364
890372
890377
890379
900672
920493
930327
930331
930575
930580
930582
930587
940425
940529
950261
950362
950367
950369
950374
960212
980496
990317
990326
990330
990334
990577
990578
991160
1000415
1010256
1010257
1010264
1010364
1010365
1010947
1020094
1020202
1050223
1050320
1050329
1070247
1070259
1080097
1100853
1110689
1120527
1120532
1120539
1120640
1160595
1160735
1160843
1170684
1170692
1180522
1180529
1180530
1180534
1180535
1180630
1190372
1210651
1220485
1220489
1220738
1230687
1240524
1240525
1250362
1280475

TABLE 1-continued

Possible Subfragment Masses.

1280484
1280967
1290222
1290805
1331013
1340957
1340962
1350217
1350791
1350795
1350800
1360055
1390750
1391003
1400952
1410786
1410790
1420624
1450753
1520382
1520483
1540169
1580377
1581052
1590215
1600164
1610002
1680810
1690648
1700597
1710435
1740805
1750643
1760592
1770430
1811212
1830999
1930757
1940595
1990752
2000590
2101023
2161018
2170852
2170856
2230842
2230851
2341117
2401120
2631275
3581642

TABLE 2

Possible Subfragment Masses Remaining After Averaging.

140149
170266
170266
170266
170266
170266
170266
180099
260029
410375
420211
420211
420461
420461
420461
420461
420461
430300
430300

TABLE 2-continued

Possible Subfragment Masses Remaining After Averaging.

| |
|---|
| 440249 |
| 460419 |
| 460419 |
| 460419 |
| 460419 |
| 470159 |
| 470257 |
| 510118 |
| 590474 |
| 590729 |
| 590729 |
| 590729 |
| 590729 |
| 600572 |
| 610514 |
| 700420 |
| 720100 |
| 720100 |
| 720207 |
| 750230 |
| 750230 |
| 760065 |
| 760065 |
| 760313 |
| 760313 |
| 770147 |
| 780097 |
| 780097 |
| 780097 |
| 780097 |
| 780097 |
| 789939 |
| 800276 |
| 810222 |
| 810222 |
| 820060 |
| 820060 |
| 820060 |
| 820060 |
| 820060 |
| 820060 |
| 840095 |
| 840095 |
| 840682 |
| 849937 |
| 860845 |
| 870592 |
| 880051 |
| 880534 |
| 880632 |
| 880885 |
| 890372 |
| 890372 |
| 890372 |
| 890372 |
| 900672 |
| 920493 |
| 930329 |
| 930329 |
| 930580 |
| 930580 |
| 930580 |
| 930580 |
| 940425 |
| 940529 |
| 950261 |
| 950367 |
| 950367 |
| 950367 |
| 950367 |
| 960212 |
| 980496 |
| 990326 |
| 990326 |
| 990326 |
| 990326 |
| 990577 |
| 990577 |

TABLE 2-continued

Possible Subfragment Masses Remaining After Averaging.

| |
|---|
| 991160 |
| 1000415 |
| 1010258 |
| 1010258 |
| 1010258 |
| 1010364 |
| 1010364 |
| 1010947 |
| 1020094 |
| 1020202 |
| 1050223 |
| 1050324 |
| 1050324 |
| 1070253 |
| 1070253 |
| 1080097 |
| 1100853 |
| 1110689 |
| 1120532 |
| 1120532 |
| 1120532 |
| 1120640 |
| 1160595 |
| 1160735 |
| 1160843 |
| 1170688 |
| 1170688 |
| 1180529 |
| 1180529 |
| 1180529 |
| 1180529 |
| 1180529 |
| 1180630 |
| 1190372 |
| 1210651 |
| 1220487 |
| 1220487 |
| 1220738 |
| 1230687 |
| 1240524 |
| 1240524 |
| 1250362 |
| 1280479 |
| 1280479 |
| 1280967 |
| 1290222 |
| 1290805 |
| 1331013 |
| 1340959 |
| 1340959 |
| 1350217 |
| 1350795 |
| 1350795 |
| 1350795 |
| 1360055 |
| 1390750 |
| 1391003 |
| 1400952 |
| 1410788 |
| 1410788 |
| 1420624 |
| 1450753 |
| 1520382 |
| 1520483 |
| 1540169 |
| 1580377 |
| 1581052 |
| 1590215 |
| 1600164 |
| 1610002 |
| 1680810 |
| 1690648 |
| 1700597 |
| 1710435 |
| 1740805 |
| 1750643 |
| 1760592 |
| 1770430 |

TABLE 2-continued

Possible Subfragment Masses Remaining After Averaging.

1811212
1830999
1930757
1940595
1990752
2000590
2101023
2161018
2170854
2170854
2230846
2230846
2341117
2401120
2631275
3581642

Now partitions (sums of subfragments) that can be obtained using the averaged subfragment masses will be found; the 4-subfragment partitions representing xemilofiban will be generated.

As previously mentioned there are 191 possible subfragments after averaging; there are 53727345 possible combinations of 191 masses taken four at a time. However, the previous step reduced the number of unique masses and sorted the listing; now it is possible to take advantage of that operation to considerably reduce the number of combinations that need to be checked as possible partitions.

Let us call the subfragments A, B, C, and D where the letters represent subfragments in increasing order of mass. A is the smallest; D is the largest. The first set of possible masses would be the first four masses in Table 2: 140149, 170266, 170266, and 170266. The "Sum" of these four masses (650947) is compared to the molecular weight, which is the last number in the listing (3581642) to check whether the difference is less than MaxDefect. If so, this set of four subfragment masses is a partition.

In this case, the difference is much greater than MaxDefect. We need to look at the next combination. The "D" subfragment is always changing most rapidly; the A subfragment changes least rapidly. The next set of four numbers would therefore be the first three masses in the listing (A, B, and C) and the fifth mass, D: 140149, 170266, 170266, and 170266, which is the same partition as the first set of four masses. Several "rules" are applied that considerably reduce the number of combinations tested and also prevent duplicate results from being generated.

1. No mass can repeat in the same position.

So the next subfragment D mass would be 180099, the eighth mass in the list of possible subfragment masses.

There are other rules which cut down the number of combinations tested. These rules rely on the listing of possible subfragment masses being in increasing order of mass. (Analogous rules could be implemented if the masses were sorted in decreasing order.)

2. The sum of the subfragments cannot exceed the upper bound which is the molecular weight plus the MaxDefect (3581659). When the sum exceeds the upper bound, then subfragment C will be moved to the next mass in the list and D will be moved back to the next mass after C.
3. The mass of C must be less than the mass of the upper bound divided by 2. When the mass of C exceeds the upper bound divided by 2, then subfragment B will be moved to the next mass in the list and C will be moved back to the next mass after B.
4. The mass of B must be less than the mass of the upper bound divided by 3. When the mass of B exceeds the upper bound divided by 3, then subfragment A will be moved to the next mass in the list and B will be moved back to the next mass after A.
5. The mass of A must be less than the mass of the upper bound divided by 4. When the mass of A exceeds the upper bound divided by 4, the search for partitions is complete.

On the next five pages, the initial combinations generated from the xemilofiban possible subfragments are listing is shown. This illustrates some of the rules above. By generating combinations in this way, only 1511940 combinations of 4 masses were generated and tested as partitions, instead of the original 322014330 total combinations of 298 masses taken 4 at a time.

| | | | |
|---|---|---|---|
| 140149 | 170266 | 170266 | 170266 |
| 140149 | 170266 | 170266 | 180099 |
| 140149 | 170266 | 170266 | 260029 |
| 140149 | 170266 | 170266 | 410375 |
| 140149 | 170266 | 170266 | 420211 |
| 140149 | 170266 | 170266 | 420461 |
| 140149 | 170266 | 170266 | 430300 |
| 140149 | 170266 | 170266 | 440249 |
| 140149 | 170266 | 170266 | 460419 |
| 140149 | 170266 | 170266 | 470159 |
| 140149 | 170266 | 170266 | 470257 |
| 140149 | 170266 | 170266 | 510118 |
| 140149 | 170266 | 170266 | 590474 |
| 140149 | 170266 | 170266 | 590729 |
| 140149 | 170266 | 170266 | 600572 |
| 140149 | 170266 | 170266 | 610514 |
| 140149 | 170266 | 170266 | 700420 |
| 140149 | 170266 | 170266 | 720100 |
| 140149 | 170266 | 170266 | 720207 |
| 140149 | 170266 | 170266 | 750230 |
| 140149 | 170266 | 170266 | 760065 |
| 140149 | 170266 | 170266 | 760313 |
| 140149 | 170266 | 170266 | 770147 |
| 140149 | 170266 | 170266 | 780097 |
| 140149 | 170266 | 170266 | 789939 |
| 140149 | 170266 | 170266 | 800276 |
| 140149 | 170266 | 170266 | 810222 |
| 140149 | 170266 | 170266 | 820060 |
| 140149 | 170266 | 170266 | 840095 |
| 140149 | 170266 | 170266 | 840682 |
| 140149 | 170266 | 170266 | 849937 |
| 140149 | 170266 | 170266 | 860845 |
| 140149 | 170266 | 170266 | 870592 |
| 140149 | 170266 | 170266 | 880051 |
| 140149 | 170266 | 170266 | 880534 |
| 140149 | 170266 | 170266 | 880632 |
| 140149 | 170266 | 170266 | 880885 |
| 140149 | 170266 | 170266 | 890372 |
| 140149 | 170266 | 170266 | 900672 |
| 140149 | 170266 | 170266 | 920493 |
| 140149 | 170266 | 170266 | 930329 |
| 140149 | 170266 | 170266 | 930580 |
| 140149 | 170266 | 170266 | 940425 |
| 140149 | 170266 | 170266 | 940529 |
| 140149 | 170266 | 170266 | 950261 |
| 140149 | 170266 | 170266 | 950367 |
| 140149 | 170266 | 170266 | 960212 |
| 140149 | 170266 | 170266 | 980496 |
| 140149 | 170266 | 170266 | 990326 |
| 140149 | 170266 | 170266 | 990577 |
| 140149 | 170266 | 170266 | 991160 |
| 140149 | 170266 | 170266 | 1000415 |
| 140149 | 170266 | 170266 | 1010258 |
| 140149 | 170266 | 170266 | 1010364 |
| 140149 | 170266 | 170266 | 1010947 |
| 140149 | 170266 | 170266 | 1020094 |
| 140149 | 170266 | 170266 | 1020202 |
| 140149 | 170266 | 170266 | 1050223 |
| 140149 | 170266 | 170266 | 1050324 |

| | | | |
|---|---|---|---|
| 140149 | 170266 | 170266 | 1070253 |
| 140149 | 170266 | 170266 | 1080097 |
| 140149 | 170266 | 170266 | 1100853 |
| 140149 | 170266 | 170266 | 1110689 |
| 140149 | 170266 | 170266 | 1120532 |
| 140149 | 170266 | 170266 | 1120640 |
| 140149 | 170266 | 170266 | 1160595 |
| 140149 | 170266 | 170266 | 1160735 |
| 140149 | 170266 | 170266 | 1160843 |
| 140149 | 170266 | 170266 | 1170688 |
| 140149 | 170266 | 170266 | 1180529 |
| 140149 | 170266 | 170266 | 1180630 |
| 140149 | 170266 | 170266 | 1190372 |
| 140149 | 170266 | 170266 | 1210651 |
| 140149 | 170266 | 170266 | 1220487 |
| 140149 | 170266 | 170266 | 1220738 |
| 140149 | 170266 | 170266 | 1230687 |
| 140149 | 170266 | 170266 | 1240524 |
| 140149 | 170266 | 170266 | 1250362 |
| 140149 | 170266 | 170266 | 1280479 |
| 140149 | 170266 | 170266 | 1280967 |
| 140149 | 170266 | 170266 | 1290222 |
| 140149 | 170266 | 170266 | 1290805 |
| 140149 | 170266 | 170266 | 1331013 |
| 140149 | 170266 | 170266 | 1340959 |
| 140149 | 170266 | 170266 | 1350217 |
| 140149 | 170266 | 170266 | 1350795 |
| 140149 | 170266 | 170266 | 1360055 |
| 140149 | 170266 | 170266 | 1390750 |
| 140149 | 170266 | 170266 | 1391003 |
| 140149 | 170266 | 170266 | 1400952 |
| 140149 | 170266 | 170266 | 1410788 |
| 140149 | 170266 | 170266 | 1420624 |
| 140149 | 170266 | 170266 | 1450753 |
| 140149 | 170266 | 170266 | 1520382 |
| 140149 | 170266 | 170266 | 1520483 |
| 140149 | 170266 | 170266 | 1540169 |
| 140149 | 170266 | 170266 | 1580377 |
| 140149 | 170266 | 170266 | 1581052 |
| 140149 | 170266 | 170266 | 1590215 |
| 140149 | 170266 | 170266 | 1600164 |
| 140149 | 170266 | 170266 | 1610002 |
| 140149 | 170266 | 170266 | 1680810 |
| 140149 | 170266 | 170266 | 1690648 |
| 140149 | 170266 | 170266 | 1700597 |
| 140149 | 170266 | 170266 | 1710435 |
| 140149 | 170266 | 170266 | 1740805 |
| 140149 | 170266 | 170266 | 1750643 |
| 140149 | 170266 | 170266 | 1760592 |
| 140149 | 170266 | 170266 | 1770430 |
| 140149 | 170266 | 170266 | 1811212 |
| 140149 | 170266 | 170266 | 1830999 |
| 140149 | 170266 | 170266 | 1930757 |
| 140149 | 170266 | 170266 | 1940595 |
| 140149 | 170266 | 170266 | 1990752 |
| 140149 | 170266 | 170266 | 2000590 |
| 140149 | 170266 | 170266 | 2101023 |
| 140149 | 170266 | 170266 | 2161018 |
| 140149 | 170266 | 170266 | 2170854 |
| 140149 | 170266 | 170266 | 2230846 |
| 140149 | 170266 | 170266 | 2341117 |
| 140149 | 170266 | 170266 | 2401120 |
| 140149 | 170266 | 170266 | 2631275 |
| 140149 | 170266 | 180099 | 260029 |
| 140149 | 170266 | 180099 | 410375 |
| 140149 | 170266 | 180099 | 420211 |
| 140149 | 170266 | 180099 | 420461 |
| 140149 | 170266 | 180099 | 430300 |
| 140149 | 170266 | 180099 | 440249 |
| 140149 | 170266 | 180099 | 460419 |
| 140149 | 170266 | 180099 | 470159 |
| 140149 | 170266 | 180099 | 470257 |
| 140149 | 170266 | 180099 | 510118 |
| 140149 | 170266 | 180099 | 590474 |
| 140149 | 170266 | 180099 | 590729 |
| 140149 | 170266 | 180099 | 600572 |
| 140149 | 170266 | 180099 | 610514 |
| 140149 | 170266 | 180099 | 700420 |
| 140149 | 170266 | 180099 | 720100 |
| 140149 | 170266 | 180099 | 720207 |
| 140149 | 170266 | 180099 | 750230 |
| 140149 | 170266 | 180099 | 760065 |
| 140149 | 170266 | 180099 | 760313 |
| 140149 | 170266 | 180099 | 770147 |
| 140149 | 170266 | 180099 | 780097 |
| 140149 | 170266 | 180099 | 789939 |
| 140149 | 170266 | 180099 | 800276 |
| 140149 | 170266 | 180099 | 810222 |
| 140149 | 170266 | 180099 | 820060 |
| 140149 | 170266 | 180099 | 840095 |
| 140149 | 170266 | 180099 | 840682 |
| 140149 | 170266 | 180099 | 849937 |
| 140149 | 170266 | 180099 | 860845 |
| 140149 | 170266 | 180099 | 870592 |
| 140149 | 170266 | 180099 | 880051 |
| 140149 | 170266 | 180099 | 880534 |
| 140149 | 170266 | 180099 | 880632 |
| 140149 | 170266 | 180099 | 880885 |
| 140149 | 170266 | 180099 | 890372 |
| 140149 | 170266 | 180099 | 900672 |
| 140149 | 170266 | 180099 | 920493 |
| 140149 | 170266 | 180099 | 930329 |
| 140149 | 170266 | 180099 | 930580 |
| 140149 | 170266 | 180099 | 940425 |
| 140149 | 170266 | 180099 | 940529 |
| 140149 | 170266 | 180099 | 950261 |
| 140149 | 170266 | 180099 | 950367 |
| 140149 | 170266 | 180099 | 960212 |
| 140149 | 170266 | 180099 | 980496 |
| 140149 | 170266 | 180099 | 990326 |
| 140149 | 170266 | 180099 | 990577 |
| 140149 | 170266 | 180099 | 991160 |
| 140149 | 170266 | 180099 | 1000415 |
| 140149 | 170266 | 180099 | 1010258 |
| 140149 | 170266 | 180099 | 1010364 |
| 140149 | 170266 | 180099 | 1010947 |
| 140149 | 170266 | 180099 | 1020094 |
| 140149 | 170266 | 180099 | 1020202 |
| 140149 | 170266 | 180099 | 1050223 |
| 140149 | 170266 | 180099 | 1050324 |
| 140149 | 170266 | 180099 | 1070253 |
| 140149 | 170266 | 180099 | 1080097 |
| 140149 | 170266 | 180099 | 1100853 |
| 140149 | 170266 | 180099 | 1110689 |
| 140149 | 170266 | 180099 | 1120532 |
| 140149 | 170266 | 180099 | 1120640 |
| 140149 | 170266 | 180099 | 1160595 |
| 140149 | 170266 | 180099 | 1160735 |
| 140149 | 170266 | 180099 | 1160843 |
| 140149 | 170266 | 180099 | 1170688 |
| 140149 | 170266 | 180099 | 1180529 |
| 140149 | 170266 | 180099 | 1180630 |
| 140149 | 170266 | 180099 | 1190372 |
| 140149 | 170266 | 180099 | 1210651 |
| 140149 | 170266 | 180099 | 1220487 |
| 140149 | 170266 | 180099 | 1220738 |
| 140149 | 170266 | 180099 | 1230687 |
| 140149 | 170266 | 180099 | 1240524 |
| 140149 | 170266 | 180099 | 1250362 |
| 140149 | 170266 | 180099 | 1280479 |
| 140149 | 170266 | 180099 | 1280967 |
| 140149 | 170266 | 180099 | 1290222 |
| 140149 | 170266 | 180099 | 1290805 |
| 140149 | 170266 | 180099 | 1331013 |
| 140149 | 170266 | 180099 | 1340959 |
| 140149 | 170266 | 180099 | 1350217 |
| 140149 | 170266 | 180099 | 1350795 |
| 140149 | 170266 | 180099 | 1360055 |
| 140149 | 170266 | 180099 | 1390750 |
| 140149 | 170266 | 180099 | 1391003 |
| 140149 | 170266 | 180099 | 1400952 |
| 140149 | 170266 | 180099 | 1410788 |
| 140149 | 170266 | 180099 | 1420624 |
| 140149 | 170266 | 180099 | 1450753 |
| 140149 | 170266 | 180099 | 1520382 |
| 140149 | 170266 | 180099 | 1520483 |
| 140149 | 170266 | 180099 | 1540169 |
| 140149 | 170266 | 180099 | 1580377 |
| 140149 | 170266 | 180099 | 1581052 |
| 140149 | 170266 | 180099 | 1590215 |

-continued

| | | | |
|---|---|---|---|
| 140149 | 170266 | 180099 | 1600164 |
| 140149 | 170266 | 180099 | 1610002 |
| 140149 | 170266 | 180099 | 1680810 |
| 140149 | 170266 | 180099 | 1690648 |
| 140149 | 170266 | 180099 | 1700597 |
| 140149 | 170266 | 180099 | 1710435 |
| 140149 | 170266 | 180099 | 1740805 |
| 140149 | 170266 | 180099 | 1750643 |
| 140149 | 170266 | 180099 | 1760592 |
| 140149 | 170266 | 180099 | 1770430 |
| 140149 | 170266 | 180099 | 1811212 |
| 140149 | 170266 | 180099 | 1830999 |
| 140149 | 170266 | 180099 | 1930757 |
| 140149 | 170266 | 180099 | 1940595 |
| 140149 | 170266 | 180099 | 1990752 |
| 140149 | 170266 | 180099 | 2000590 |
| 140149 | 170266 | 180099 | 2101023 |
| 140149 | 170266 | 180099 | 2161018 |
| 140149 | 170266 | 180099 | 2170854 |
| 140149 | 170266 | 180099 | 2230846 |
| 140149 | 170266 | 180099 | 2341117 |
| 140149 | 170266 | 180099 | 2401120 |
| 140149 | 170266 | 180099 | 2631275 |
| 140149 | 170266 | 260029 | 410375 |
| 140149 | 170266 | 260029 | 420211 |

At this point, the sets of 4 subfragment masses that are partitions of the molecular weight have been found (A+B+C+D=molecular weight). Some of these partitions will account for the accurate-mass fragmentation data better than others. The partitions are now scored by checking the neutralized fragment masses obtained on a mass spectrometer against "subsums" of each partition, and a score is calculated for each partition. There are 14 of these subsums listed below.

A
B
C
D
A+B
A+C
A+D
B+C
B+D
C+D
A+B+C
A+B+D
A+C+D
B+C+D

Based on its intensity, each neutralized fragment ion has been assigned a coverage value (Sweeney 2003). If the difference between the mass of a subsum and the mass of a neutralized fragment ion is within the MaxDefect window, then the score of that partition is incremented by the coverage value of that neutralized fragment ion. In addition, if any two subfragments of a partition are always assigned in the same way, that partition is considered "linked" (Sweeney 2003) and that partition is given a score of zero.

Partitions for xemilofiban accurate-mass fragmentation data having a score greater than 50 are shown below. The bolded partitions are those that are most consistent with the structure of xemilofiban; the bolded partition in the sixth line is consistent with the Drawing:

| | | | |
|---|---|---|---|
| 460419 (blue) | 820060 (orange) | 950367 (magenta) | 1350795 (green). |

Total Combinations of Four Masses: 1511940 Partitions total: 2744

| Score | A | B | C | D |
|---|---|---|---|---|
| 73 | 170266 | 820060 | 1180529 | 1410788 |
| 61 | 170266 | 820060 | 1240524 | 1350795 |
| 61 | 420211 | 820060 | 930580 | 1410788 |
| 61 | 420461 | 820060 | 930329 | 1410788 |
| 61 | 420461 | 820060 | 990326 | 1350795 |
| 73 | 460419 | 820060 | 950367 | 1350795 |
| 58 | 590729 | 760065 | 820060 | 1410788 |
| 58 | 590729 | 820060 | 820060 | 1350795 |
| 61 | 600572 | 750230 | 820060 | 1410788 |
| 61 | 600572 | 810222 | 820060 | 1350795 |

The search time is 71 milliseconds using the new art, which is about 150 times faster than the prior art.

CONCLUSIONS, RAMIFICATIONS, AND SCOPE

1. Looking at the two partitions above that had the highest score (both 73) it appears that these two partitions are related. The 1410788 in the first one could be replaced with the 950367 and 460419 of the other, and the 1350795 in the second one could be replaced by the 1180529 and 170266 of the first one. Both 4-subfragment partitions would then end up as an identical 5-subfragment partition:

| | | | | |
|---|---|---|---|---|
| 170266 | 460419 | 820060 | 950367 | 1180529 |

Normally a great deal more time is required to generate 5-subfragment partitions than 4-subfragment partitions using the invention or prior art outlined above. A ramification of the invention is to only use subfragment masses of the best matches from 2, 3, and 4-subfragment partitions to generate 5-subfragment and higher partitions, while using the same process.

Using xemilofiban as an example, generating a new list from the subfragments of the best ten 4-subfragment partitions above, there are only 40 subfragment masses in the new list. Using these 40 masses and adding an analogous 5-subfragment function to the program, the following results were obtained (in addition to the previous 4-subfragment results):

Total Combinations of Five Masses: 6279 Partitions total: 34

| Score | A | B | C | D | E |
|---|---|---|---|---|---|
| 76 | 170266 | 170266 | 820060 | 1180529 | 1240524 |
| 76 | 170266 | 420461 | 820060 | 990326 | 1180529 |
| 88 | 170266 | 460419 | 820060 | 950367 | 1180529 |
| 73 | 170266 | 590729 | 760065 | 820060 | 1240524 |
| 73 | 170266 | 590729 | 820060 | 820060 | 1180529 |
| 76 | 420211 | 460419 | 820060 | 930580 | 950367 |
| 76 | 420461 | 460419 | 820060 | 930329 | 950367 |
| 76 | 420461 | 590729 | 760065 | 820060 | 990326 |

As the results show, higher scoring 5-subfragment partitions were found that basically combine some 4-subfragment solutions. Adding 5-subfragments in this fashion did not noticeably increase the total CPU time; it was still 71 milliseconds.

2. One can take into account that some assignments are logically inconsistent. For example, there were six possible subsums of two subfragments above. Assuming there is no overall cyclic structure, four subfragments can only be arranged in space in two ways (Sweeney 2003), and neither arrangement will permit more than three pairs of subfragments to be connected together. Therefore, any 4-subfragment partition assigning more than three subsum pairs can be dropped, without attempting to arrange the subfragments in space. Similar logic can be applied to arrangements of larger numbers of subfragments (e.g. 5-subfragment partitions).
3. Another ramification is that the process described in this invention is much simpler in terms of the number of registers required than the prior art. This would make it suited for implementing a parallel version using parallel approaches such as CUDA with GPU processors, which have more limited registers than CPU processors.
4. It would be advantageous with some mass spectrometers to have a MaxDefect window that is not a constant; it could vary over the mass range.
5. Although the example shown here was based on CID type mass spectral data, the invention should also be applicable to accurate mass fragments generated by EI (electron ionization) or other fragmentation techniques.

DEFINITIONS

Accurate-mass mass spectral data: mass spectral data that is accurate to 10 ppm accuracy or better, generally represented as a four or five decimal-place rational number.

Accurate-mass fragmentation data: accurate-mass spectral fragmentation data arising from collision-induced dissociation (collisionally activated dissociation) of a parent ion into smaller ions. This spectral data including, but not limited to, in-source fragmentation, MS/MS fragmentation, and MSn fragmentation.

EI mass spectral data: mass spectral fragmentation data arising from electron ionization FT-ICR mass spectrometer: Fourier transform ion-cyclotron resonance mass spectrometer, also known as FTMS.

fragment ion: a set of connected atoms arising from the cleavage of an organic compound in a mass spectrometer.

heavy atom: a non-hydrogen atom known compound: an organic compound that has been identified and documented in a database or databases.

modular structure: a representation of an organic compound as a small number of unbreakable subfragments, of known elemental composition, joined together in a two-dimensional spatial arrangement.

molecular structure: a two-dimensional representation (drawing) of an organic compound.

MSMS: (mass spectrometry—mass spectrometry or MS/MS) a mass spectral technique that produces fragment ions from a precursor ion, by using an instrument that is tandem in time or tandem in space.

MS$^n$: any mass spectral technique that produces fragment ions of fragment ions, where n−1 indicates the number of levels of fragmentation.

neutralized fragment ion: a fragment that would result if a proton were added or removed in order to neutralize the charge on a molecule or fragment ion.

novel compound: a compound that has not been documented previously partition: mathematically, a partition is a set of integers that sums up to another integer. Here the term partition is used to describe a set of masses summing to a mass within the MaxDefect window of the molecular weight.

partitioning: the process for deriving the masses of subfragments from mass spectral fragmentation data of a compound; the masses of the subfragments of a partition will sum to a mass within the MaxDefect window of the molecular weight.

seam: a breakable connection point between subfragments of a modular structure subfragment: a set of connected atoms that make up one unit of a modular structure subgroup: a set of connected atoms, derived from a computerized molecular structure, that make up one unit of multiple complementary units comprising the entire molecule.

subsum: a sum of one combination of subfragment masses template: a known compound with well-understood mass spectral fragmentation that is used to identify related unknown compounds from their fragment ions.

unknown compound: a compound under investigation that will prove to be either a known compound or a novel compound.

plausible mass: theoretical masses of combinations of elements of carbon, hydrogen, nitrogen, oxygen, sulfur, phosphorus, chlorine, bromine, and fluorine that can represent subfragments of actual molecules.

APPENDIX

| List of Plausible Masses | |
| --- | --- |
| 14.0157 | CH2 |
| 15.0109 | HN |
| 15.0235 | CH3 |
| 15.9949 | O |
| 16.0187 | H2N |
| 17.0027 | HO |
| 17.0265 | H3N |
| 18.0106 | H2O |
| 18.9984 | F |
| 20.0062 | HF |
| 26.0031 | CN |
| 26.0157 | C2H2 |
| 27.0109 | CHN |
| 27.0235 | C2H3 |
| 27.9949 | CO |
| 28.0061 | N2 |
| 28.0187 | CH2N |
| 28.0313 | C2H4 |
| 29.0027 | CHO |
| 29.0140 | HN2 |
| 29.0265 | CH3N |
| 29.0391 | C2H5 |
| 29.9980 | NO |
| 30.0106 | CH2O |
| 30.0218 | H2N2 |
| 30.0344 | CH4N |
| 31.0058 | HNO |
| 31.0184 | CH3O |
| 31.0296 | H3N2 |
| 31.0422 | CH5N |
| 32.0062 | CHF |
| 31.9898 | O2 |
| 32.0136 | H2NO |
| 32.0262 | CH4O |
| 32.0374 | H4N2 |
| 32.9977 | HO2 |
| 33.0141 | CH2F |
| 32.9799 | HS |
| 33.0215 | H3NO |
| 33.9972 | H3P |
| 34.0055 | H2O2 |
| 33.9877 | H2S |
| 34.0219 | CH3F |
| 34.9689 | Cl |
| 35.9767 | HCl |

APPENDIX-continued

List of Plausible Masses

| Mass | Formula |
|---|---|
| 38.0157 | C3H2 |
| 39.0109 | C2HN |
| 39.0235 | C3H3 |
| 39.9949 | C2O |
| 40.0061 | CN2 |
| 40.0187 | C2H2N |
| 40.0313 | C3H4 |
| 41.0027 | C2HO |
| 41.0140 | CHN2 |
| 41.0265 | C2H3N |
| 41.0391 | C3H5 |
| 41.9980 | CNO |
| 42.0092 | N3 |
| 42.0106 | C2H2O |
| 42.0218 | CH2N2 |
| 42.0344 | C2H4N |
| 42.0470 | C3H6 |
| 43.0058 | CHNO |
| 43.0170 | HN3 |
| 43.0184 | C2H3O |
| 43.0296 | CH3N2 |
| 43.0422 | C2H5N |
| 43.0548 | C3H7 |
| 43.9721 | CS |
| 43.9898 | CO2 |
| 44.0011 | N2O |
| 44.0136 | CH2NO |
| 44.0249 | H2N3 |
| 44.0262 | C2H4O |
| 44.0374 | CH4N2 |
| 44.0500 | C2H6N |
| 44.0626 | C3H8 |
| 44.9977 | CHO2 |
| 45.0089 | HN2O |
| 45.0141 | C2H2F |
| 44.9799 | CHS |
| 45.0215 | CH3NO |
| 45.0327 | H3N3 |
| 45.0340 | C2H5O |
| 45.0453 | CH5N2 |
| 45.0578 | C2H7N |
| 46.0055 | CH2O2 |
| 45.9929 | NO2 |
| 45.9877 | CH2S |
| 46.0167 | H2N2O |
| 46.0219 | C2H3F |
| 46.0293 | CH4NO |
| 46.0405 | H4N3 |
| 46.0419 | C2H6O |
| 46.0531 | CH6N2 |
| 46.9830 | HNS |
| 46.9955 | CH3S |
| 47.0007 | HNO2 |
| 47.0133 | CH3O2 |
| 47.0171 | CH2NF |
| 47.0245 | H3N2O |
| 47.0297 | C2H4F |
| 47.0371 | CH5NO |
| 49.9826 | H2OS |
| 49.9923 | CH3Cl |
| 49.9968 | CF2 |
| 50.0157 | C4H2 |
| 50.0168 | CH3OF |
| 51.0046 | CHF2 |
| 51.0109 | C3HN |
| 51.9949 | C3O |
| 52.0061 | C2N2 |
| 52.0125 | CH2F2 |
| 52.0187 | C3H2N |
| 52.0313 | C4H4 |
| 54.0106 | C3H2O |
| 54.0218 | C2H2N2 |
| 54.0470 | C4H6 |
| 55.0058 | C2HNO |
| 55.0170 | CHN3 |
| 55.0184 | C3H3O |
| 55.0296 | C2H3N2 |
| 55.0422 | C3H5N |
| 55.0548 | C4H7 |
| 55.9721 | C2S |
| 55.9898 | C2O2 |
| 56.0011 | CN2O |
| 56.0062 | C3HF |
| 56.0123 | N4 |
| 56.0136 | C2H2NO |
| 56.0249 | CH2N3 |
| 56.0262 | C3H4O |
| 56.0374 | C2H4N2 |
| 56.0500 | C3H6N |
| 56.0626 | C4H8 |
| 56.9799 | C2HS |
| 56.9977 | C2HO2 |
| 57.0089 | CHN2O |
| 57.0141 | C3H2F |
| 57.0215 | C2H3NO |
| 57.0327 | CH3N3 |
| 57.0340 | C3H5O |
| 57.0453 | C2H5N2 |
| 57.0578 | C3H7N |
| 58.0055 | C2H2O2 |
| 57.9929 | CNO2 |
| 58.0093 | C2HNF |
| 57.9877 | C2H2S |
| 58.0167 | CH2N2O |
| 58.0219 | C3H3F |
| 58.0279 | H2N4 |
| 58.0293 | C2H4NO |
| 58.0405 | CH4N3 |
| 58.0419 | C3H6O |
| 58.0531 | C2H6N2 |
| 58.0657 | C3H8N |
| 58.0783 | C4H10 |
| 58.9830 | CHNS |
| 58.9925 | CH2NP |
| 58.9955 | C2H3S |
| 59.0007 | CHNO2 |
| 59.0120 | HN3O |
| 59.0133 | C2H3O2 |
| 59.0171 | C2H2NF |
| 59.0245 | CH3N2O |
| 59.0297 | C3H4F |
| 59.0371 | C2H5NO |
| 59.0483 | CH5N3 |
| 59.0497 | C3H7O |
| 59.0609 | C2H7N2 |
| 59.0735 | C3H9N |
| 59.9670 | COS |
| 59.9767 | C2HCl |
| 59.9847 | CO3 |
| 59.9908 | CH2NS |
| 59.9960 | N2O2 |
| 60.0003 | CH3NP |
| 60.0011 | C2HOF |
| 60.0086 | CH2NO2 |
| 60.0124 | CHN2F |
| 60.0198 | H2N3O |
| 60.0211 | C2H4O2 |
| 60.0250 | C2H3NF |
| 60.0324 | CH4N2O |
| 60.0375 | C3H5F |
| 60.0436 | H4N4 |
| 60.0449 | C2H6NO |
| 60.0562 | CH6N3 |
| 60.0575 | C3H8O |
| 60.0687 | C2H8N2 |
| 60.9845 | C2H2Cl |
| 60.9926 | CHO3 |
| 61.0038 | HN2O2 |
| 61.0090 | C2H2OF |
| 61.0164 | CH3NO2 |
| 61.0202 | CH2N2F |
| 61.0290 | C2H5O2 |
| 61.0328 | C2H4NF |
| 61.0402 | CH5N2O |
| 61.0454 | C3H6F |
| 61.0528 | C2H7NO |

APPENDIX-continued

List of Plausible Masses

| | |
|---|---|
| 61.0640 | CH7N3 |
| 62.0004 | CH2O3 |
| 61.9968 | C2F2 |
| 61.9923 | C2H3Cl |
| 62.0116 | H2N2O2 |
| 61.9878 | NO3 |
| 62.0157 | C5H2 |
| 62.0168 | C2H3OF |
| 62.0242 | CH4NO2 |
| 62.0280 | CH3N2F |
| 62.0354 | H4N3O |
| 62.0368 | C2H6O2 |
| 62.0406 | C2H5NF |
| 62.0480 | CH6N2O |
| 62.0532 | C3H7F |
| 62.9638 | COCl |
| 62.9779 | HNOS |
| 62.9876 | CH2NCl |
| 62.9882 | CO2F |
| 62.9956 | HNO3 |
| 63.0002 | C2H4Cl |
| 63.0046 | C2HF2 |
| 63.0082 | CH3O3 |
| 63.0109 | C4HN |
| 63.0120 | CH2NOF |
| 63.0195 | H3N2O2 |
| 63.0233 | H2N3F |
| 63.0235 | C5H3 |
| 63.0246 | C2H4OF |
| 63.0320 | CH5NO2 |
| 63.0359 | CH4N2F |
| 63.0484 | C2H6NF |
| 63.9619 | O2S |
| 63.9714 | HO2P |
| 63.9716 | CHOCl |
| 63.9949 | C4O |
| 63.9954 | CH3NCl |
| 63.9961 | CHO2F |
| 64.0035 | H2NO3 |
| 64.0061 | C3N2 |
| 64.0080 | C2H5Cl |
| 64.0125 | C2H2F2 |
| 64.0160 | CH4O3 |
| 64.0187 | C4H2N |
| 64.0199 | CH3NOF |
| 64.0273 | H4N2O2 |
| 64.0311 | H3N3F |
| 64.0313 | C5H4 |
| 64.0324 | C2H5OF |
| 64.0437 | CH5N2F |
| 64.9697 | HO2S |
| 64.9907 | H2N2Cl |
| 65.0027 | C4HO |
| 65.0032 | CH4NCl |
| 65.0039 | CH2O2F |
| 65.0077 | CHNF2 |
| 65.0113 | H3NO3 |
| 65.0140 | C3HN2 |
| 65.0151 | H2N2OF |
| 65.0203 | C2H3F2 |
| 65.0265 | C4H3N |
| 65.0277 | CH4NOF |
| 65.0389 | H4N3F |
| 65.0391 | C5H5 |
| 65.9673 | CFCl |
| 65.9872 | CH3OCl |
| 65.9917 | COF2 |
| 65.9980 | C3NO |
| 66.0092 | C2N3 |
| 66.0106 | C4H2O |
| 66.0117 | CH3O2F |
| 66.0155 | CH2NF2 |
| 66.0218 | C3H2N2 |
| 66.0229 | H3N2OF |
| 66.0281 | C2H4F2 |
| 66.0344 | C4H4N |
| 66.0470 | C5H6 |
| 66.9995 | CHOF2 |
| 66.9984 | C4F |
| 67.0058 | C3HNO |
| 67.0170 | C2HN3 |
| 67.0184 | C4H3O |
| 67.0234 | CH3NF2 |
| 66.9751 | CHFCl |
| 67.0296 | C3H3N2 |
| 67.0422 | C4H5N |
| 67.0548 | C5H7 |
| 67.9829 | CH2FCl |
| 67.9898 | C3O2 |
| 68.0011 | C2N2O |
| 68.0062 | C4HF |
| 68.0074 | CH2OF2 |
| 68.0136 | C3H2NO |
| 68.0249 | C2H2N3 |
| 68.0262 | C4H4O |
| 68.0374 | C3H4N2 |
| 68.0500 | C4H6N |
| 68.0626 | C5H8 |
| 68.9952 | CF3 |
| 68.9977 | C3HO2 |
| 69.0015 | C3NF |
| 69.0089 | C2HN2O |
| 69.0141 | C4H2F |
| 69.0201 | CHN4 |
| 69.0215 | C3H3NO |
| 69.0327 | C2H3N3 |
| 69.0340 | C4H5O |
| 69.0453 | C3H5N2 |
| 69.0578 | C4H7N |
| 69.0704 | C5H9 |
| 69.9377 | Cl2 |
| 69.9929 | C2NO2 |
| 70.0030 | CHF3 |
| 70.0041 | CN3O |
| 70.0055 | C3H2O2 |
| 70.0093 | C3HNF |
| 70.0167 | C2H2N2O |
| 70.0219 | C4H3F |
| 70.0279 | CH2N4 |
| 70.0293 | C3H4NO |
| 70.0405 | C2H4N3 |
| 70.0419 | C4H6O |
| 70.0531 | C3H6N2 |
| 70.0657 | C4H8N |
| 70.0783 | C5H10 |
| 70.9689 | C3Cl |
| 70.9933 | C3OF |
| 71.0007 | C2HNO2 |
| 71.0046 | C2N2F |
| 71.0120 | CHN3O |
| 71.0133 | C3H3O2 |
| 71.0171 | C3H2NF |
| 71.0245 | C2H3N2O |
| 71.0297 | C4H4F |
| 71.0358 | CH3N4 |
| 71.0371 | C3H5NO |
| 71.0483 | C2H5N3 |
| 71.0497 | C4H7O |
| 71.0609 | C3H7N2 |
| 71.0735 | C4H9N |
| 71.0861 | C5H11 |
| 71.9767 | C3HCl |
| 71.9847 | C2O3 |
| 71.9960 | CN2O2 |
| 72.0000 | C6 |
| 72.0011 | C3HOF |
| 72.0086 | C2H2NO2 |
| 72.0124 | C2HN2F |
| 72.0198 | CH2N3O |
| 72.0211 | C3H4O2 |
| 72.0250 | C3H3NF |
| 72.0324 | C2H4N2O |
| 72.0375 | C4H5F |
| 72.0436 | CH4N4 |
| 72.0449 | C3H6NO |
| 72.0562 | C2H6N3 |

APPENDIX-continued

List of Plausible Masses

| | |
|---|---|
| 72.0575 | C4H8O |
| 72.0687 | C3H8N2 |
| 72.0813 | C4H10N |
| 72.0939 | C5H12 |
| 72.9719 | C2NCl |
| 72.9845 | C3H2Cl |
| 72.9926 | C2HO3 |
| 72.9964 | C2NOF |
| 73.0038 | CHN2O2 |
| 73.0076 | CN3F |
| 73.0078 | C6H |
| 73.0090 | C3H2OF |
| 73.0164 | C2H3NO2 |
| 73.0202 | C2H2N2F |
| 73.0276 | CH3N3O |
| 73.0290 | C3H5O2 |
| 73.0328 | C3H4NF |
| 73.0388 | H3N5 |
| 73.0402 | C2H5N2O |
| 73.0454 | C4H6F |
| 73.0514 | CH5N4 |
| 73.0528 | C3H7NO |
| 73.0640 | C2H7N3 |
| 73.0653 | C4H9O |
| 73.0766 | C3H9N2 |
| 73.0891 | C4H11N |
| 73.9798 | C2HNCl |
| 73.9878 | CNO3 |
| 73.9923 | C3H3Cl |
| 73.9968 | C3F2 |
| 74.0004 | C2H2O3 |
| 74.0031 | C5N |
| 74.0042 | C2HNOF |
| 74.0116 | CH2N2O2 |
| 74.0155 | CHN3F |
| 74.0157 | C6H2 |
| 74.0168 | C3H3OF |
| 74.0229 | H2N4O |
| 74.0242 | C2H4NO2 |
| 74.0280 | C2H3N2F |
| 74.0354 | CH4N3O |
| 74.0368 | C3H6O2 |
| 74.0406 | C3H5NF |
| 74.0480 | C2H6N2O |
| 74.0532 | C4H7F |
| 74.0592 | CH6N4 |
| 74.0606 | C3H8NO |
| 74.0718 | C2H8N3 |
| 74.0732 | C4H10O |
| 74.0844 | C3H10N2 |
| 74.9638 | C2OCl |
| 74.9750 | CN2Cl |
| 74.9876 | C2H2NCl |
| 74.9882 | C2O2F |
| 74.9956 | CHNO3 |
| 74.9995 | CN2OF |
| 75.0002 | C3H4Cl |
| 75.0046 | C3HF2 |
| 75.0082 | C2H3O3 |
| 75.0109 | C5HN |
| 75.0120 | C2H2NOF |
| 75.0195 | CH3N2O2 |
| 75.0233 | CH2N3F |
| 75.0235 | C6H3 |
| 75.0246 | C3H4OF |
| 75.0307 | H3N4O |
| 75.0320 | C2H5NO2 |
| 75.0359 | C2H4N2F |
| 75.0433 | CH5N3O |
| 75.0446 | C3H7O2 |
| 75.0484 | C3H6NF |
| 75.0558 | C2H7N2O |
| 75.0610 | C4H8F |
| 75.0671 | CH7N4 |
| 75.0684 | C3H9NO |
| 75.0796 | C2H9N3 |
| 75.9716 | C2HOCl |
| 75.9828 | CHN2Cl |
| 75.9949 | C5O |
| 75.9954 | C2H3NCl |
| 75.9961 | C2HO2F |
| 75.9999 | C2NF2 |
| 76.0035 | CH2NO3 |
| 76.0061 | C4N2 |
| 76.0073 | CHN2OF |
| 76.0080 | C3H5Cl |
| 76.0125 | C3H2F2 |
| 76.0147 | H2N3O2 |
| 76.0160 | C2H4O3 |
| 76.0185 | HN4F |
| 76.0187 | C5H2N |
| 76.0199 | C2H3NOF |
| 76.0273 | CH4N2O2 |
| 76.0311 | CH3N3F |
| 76.0313 | C6H4 |
| 76.0324 | C3H5OF |
| 76.0399 | C2H6NO2 |
| 76.0437 | C2H5N2F |
| 76.0511 | CH6N3O |
| 76.0524 | C3H8O2 |
| 76.0563 | C3H7NF |
| 76.0623 | H6N5 |
| 76.0637 | C2H8N2O |
| 76.0688 | C4H9F |
| 76.0749 | CH8N4 |
| 76.9794 | C2H2OCl |
| 76.9875 | CHO4 |
| 76.9907 | CH2N2Cl |
| 76.9913 | CNO2F |
| 76.9987 | HN2O3 |
| 77.0027 | C5HO |
| 77.0032 | C2H4NCl |
| 77.0039 | C2H2O2F |
| 77.0077 | C2HNF2 |
| 77.0113 | CH3NO3 |
| 77.0140 | C4HN2 |
| 77.0151 | CH2N2OF |
| 77.0158 | C3H6Cl |
| 77.0203 | C3H3F2 |
| 77.0225 | H3N3O2 |
| 77.0239 | C2H5O3 |
| 77.0265 | C5H3N |
| 77.0277 | C2H4NOF |
| 77.0351 | CH5N2O2 |
| 77.0389 | CH4N3F |
| 77.0391 | C6H5 |
| 77.0403 | C3H6OF |
| 77.0477 | C2H7NO2 |
| 77.0515 | C2H6N2F |
| 77.0589 | CH7N3O |
| 77.0641 | C3H8NF |
| 77.9673 | C2FCl |
| 77.9872 | C2H3OCl |
| 77.9917 | C2OF2 |
| 77.9953 | CH2O4 |
| 77.9980 | C4NO |
| 77.9985 | CH3N2Cl |
| 77.9991 | CHNO2F |
| 78.0030 | CN2F2 |
| 78.0065 | H2N2O3 |
| 78.0092 | C3N3 |
| 78.0106 | C5H2O |
| 78.0111 | C2H5NCl |
| 78.0117 | C2H3O2F |
| 78.0155 | C2H2NF2 |
| 78.0191 | CH4NO3 |
| 78.0218 | C4H2N2 |
| 78.0229 | CH3N2OF |
| 78.0236 | C3H7Cl |
| 78.0281 | C3H4F2 |
| 78.0304 | H4N3O2 |
| 78.0317 | C2H6O3 |
| 78.0344 | C5H4N |
| 78.0355 | C2H5NOF |
| 78.0429 | CH6N2O2 |
| 78.0468 | CH5N3F |

APPENDIX-continued

List of Plausible Masses

| | |
|---|---|
| 78.0470 | C6H6 |
| 78.0481 | C3H7OF |
| 78.0542 | H6N4O |
| 78.0593 | C2H7N2F |
| 78.9183 | Br |
| 78.9407 | OPS |
| 78.9585 | O3P |
| 78.9587 | CO2Cl |
| 78.9751 | C2HFCl |
| 78.9825 | CH2NOCl |
| 78.9951 | C2H4OCl |
| 78.9984 | C5F |
| 78.9995 | C2HOF2 |
| 79.0031 | CH3O4 |
| 79.0058 | C4HNO |
| 79.0063 | CH4N2Cl |
| 79.0070 | CH2NO2F |
| 79.0108 | CHN2F2 |
| 79.0144 | H3N2O3 |
| 79.0170 | C3HN3 |
| 79.0184 | C5H3O |
| 79.0189 | C2H6NCl |
| 79.0195 | C2H4O2F |
| 79.0234 | C2H3NF2 |
| 79.0269 | CH5NO3 |
| 79.0296 | C4H3N2 |
| 79.0308 | CH4N2OF |
| 79.0359 | C3H5F2 |
| 79.0382 | H5N3O2 |
| 79.0422 | C5H5N |
| 79.0433 | C2H6NOF |
| 79.0546 | CH6N3F |
| 79.0548 | C6H7 |
| 79.9262 | HBr |
| 79.9568 | O3S |
| 79.9665 | CHO2Cl |
| 79.9829 | C2H2FCl |
| 79.9898 | C4O2 |
| 79.9903 | CH3NOCl |
| 79.9910 | CHO3F |
| 79.9984 | H2NO4 |
| 80.0011 | C3N2O |
| 80.0029 | C2H5OCl |
| 80.0062 | C5HF |
| 80.0074 | C2H2OF2 |
| 80.0110 | CH4O4 |
| 80.0123 | C2N4 |
| 80.0136 | C4H2NO |
| 80.0141 | CH5N2Cl |
| 80.0148 | CH3NO2F |
| 80.0186 | CH2N2F2 |
| 80.0222 | H4N2O3 |
| 80.0249 | C3H2N3 |
| 80.0262 | C5H4O |
| 80.0274 | C2H5O2F |
| 80.0312 | C2H4NF2 |
| 80.0374 | C4H4N2 |
| 80.0386 | CH5N2OF |
| 80.0438 | C3H6F2 |
| 80.0500 | C5H6N |
| 80.0626 | C6H8 |
| 80.9743 | CH2O2Cl |
| 80.9907 | C2H3FCl |
| 80.9952 | C2F3 |
| 80.9977 | C4HO2 |
| 80.9981 | CH4NOCl |
| 80.9988 | CH2O3F |
| 81.0026 | CHNOF2 |
| 81.0089 | C3HN2O |
| 81.0141 | C5H2F |
| 81.0152 | C2H3OF2 |
| 81.0201 | C2HN4 |
| 81.0215 | C4H3NO |
| 81.0226 | CH4NO2F |
| 81.0264 | CH3N2F2 |
| 81.0327 | C3H3N3 |
| 81.0340 | C5H5O |
| 81.0390 | C2H5NF2 |
| 81.0453 | C4H5N2 |
| 81.0578 | C5H7N |
| 81.0704 | C6H9 |
| 81.9377 | CCl2 |
| 81.9622 | COFCl |
| 81.9822 | CH3O2Cl |
| 81.9929 | C3NO2 |
| 81.9986 | C2H4FCl |
| 82.0030 | C2HF3 |
| 82.0041 | C2N3O |
| 82.0055 | C4H2O2 |
| 82.0066 | CH3O3F |
| 82.0093 | C4HNF |
| 82.0167 | C3H2N2O |
| 82.0219 | C5H3F |
| 82.0230 | C2H4OF2 |
| 82.0279 | C2H2N4 |
| 82.0293 | C4H4NO |
| 82.0343 | CH4N2F2 |
| 82.0405 | C3H4N3 |
| 82.0419 | C5H6O |
| 82.0531 | C4H6N2 |
| 82.0657 | C5H8N |
| 82.0783 | C6H10 |
| 82.9455 | CHCl2 |
| 82.9689 | C4Cl |
| 82.9933 | C4OF |
| 82.9938 | CH3NFCl |
| 83.0007 | C3HNO2 |
| 83.0046 | C3N2F |
| 83.0109 | C2H2F3 |
| 83.0120 | C2HN3O |
| 83.0133 | C4H3O2 |
| 83.0171 | C4H2NF |
| 83.0183 | CH3NOF2 |
| 83.0232 | CHN5 |
| 83.0245 | C3H3N2O |
| 83.0297 | C5H4F |
| 83.0358 | C2H3N4 |
| 83.0371 | C4H5NO |
| 83.0483 | C3H5N3 |
| 83.0497 | C5H7O |
| 83.0609 | C4H7N2 |
| 83.0735 | C5H9N |
| 83.0861 | C6H11 |
| 83.9534 | CH2Cl2 |
| 83.9767 | C4HCl |
| 83.9847 | C3O3 |
| 83.9960 | C2N2O2 |
| 84.0000 | C7 |
| 84.0011 | C4HOF |
| 84.0023 | CH2O2F2 |
| 84.0061 | CHNF3 |
| 84.0072 | CN4O |
| 84.0086 | C3H2NO2 |
| 84.0124 | C3HN2F |
| 84.0135 | H2N2OF2 |
| 84.0187 | C2H3F3 |
| 84.0198 | C2H2N3O |
| 84.0211 | C4H4O2 |
| 84.0250 | C4H3NF |
| 84.0310 | CH2N5 |
| 84.0324 | C3H4N2O |
| 84.0375 | C5H5F |
| 84.0436 | C2H4N4 |
| 84.0449 | C4H6NO |
| 84.0562 | C3H6N3 |
| 84.0575 | C5H8O |
| 84.0687 | C4H8N2 |
| 84.0813 | C5H10N |
| 84.0939 | C6H12 |
| 84.9657 | CF2Cl |
| 84.9719 | C3NCl |
| 84.9845 | C4H2Cl |
| 84.9901 | COF3 |
| 84.9926 | C3HO3 |
| 84.9964 | C3NOF |
| 85.0038 | C2HN2O2 |

APPENDIX-continued

List of Plausible Masses

| | |
|---|---|
| 85.0076 | C2N3F |
| 85.0078 | C7H |
| 85.0090 | C4H2OF |
| 85.0139 | CH2NF3 |
| 85.0150 | CHN4O |
| 85.0164 | C3H3NO2 |
| 85.0202 | C3H2N2F |
| 85.0276 | C2H3N3O |
| 85.0290 | C4H5O2 |
| 85.0328 | C4H4NF |
| 85.0388 | CH3N5 |
| 85.0402 | C3H5N2O |
| 85.0454 | C5H6F |
| 85.0514 | C2H5N4 |
| 85.0528 | C4H7NO |
| 85.0640 | C3H7N3 |
| 85.0653 | C5H9O |
| 85.0766 | C4H9N2 |
| 85.0891 | C5H11N |
| 85.1017 | C6H13 |
| 24.9952 | CNH-1 |
| 25.9793 | COH-2 |
| 41.9564 | CSH-2 |

I claim:

1. A process for finding the accurate masses of subfragments of an unknown compound comprising:

a mass spectrometer capable of generating accurate-mass fragmentation data, a data processing means for determining the $0^{th}$, $1^{st}$, and $2^{nd}$ order mass differences of the fragment masses, a data processing means for eliminating $0^{th}$, $1^{st}$, and $2^{nd}$ order mass differences that have masses that are not within a MaxDefect window of masses found in a list of plausible masses, a data processing means for sorting remaining $0^{th}$, $1^{st}$, and $2^{nd}$ order mass differences in numerical order, a data processing means for replacing the remaining $0^{th}$, $1^{st}$, and $2^{nd}$ order mass differences that are within a MaxDefect window of other remaining $0^{th}$, $1^{st}$, and $2^{nd}$ order mass differences with the average mass of these mass differences, a data processing means for finding partitions that can be obtained using the averaged mass differences, a data processing means for checking the subsums of these partitions, in all combinations, against the fragment masses obtained on a mass spectrometer, ignoring linked partitions, and determining a score for the remaining partitions, whereby accurate masses of subfragments can be obtained more rapidly from accurate-mass fragmentation data.

* * * * *